United States Patent
Hulvershorn et al.

(10) Patent No.: US 10,463,838 B2
(45) Date of Patent: Nov. 5, 2019

(54) VASCULAR ACCESS METHODS AND DEVICES

(75) Inventors: Justin Hulvershorn, Seattle, WA (US); Karl Schmidt, Seattle, WA (US); Douglas Swartz, Seattle, WA (US)

(73) Assignee: Medline Industries, Inc, Northfield, IL (US)

( * ) Notice: Subject to any disclaimer, the term of this patent is extended or adjusted under 35 U.S.C. 154(b) by 1296 days.

(21) Appl. No.: 12/806,798

(22) Filed: Aug. 19, 2010

(65) Prior Publication Data
US 2011/0046477 A1 Feb. 24, 2011

Related U.S. Application Data

(60) Provisional application No. 61/235,004, filed on Aug. 19, 2009, provisional application No. 61/300,794, filed on Feb. 2, 2010.

(51) Int. Cl.
| | |
|---|---|
| *A61M 25/06* | (2006.01) |
| *A61B 5/0215* | (2006.01) |
| *A61B 5/00* | (2006.01) |
| *A61M 5/42* | (2006.01) |
| *A61B 90/00* | (2016.01) |

(Continued)

(52) U.S. Cl.
CPC .......... *A61M 25/06* (2013.01); *A61B 5/0215* (2013.01); *A61B 5/489* (2013.01); *A61B 5/4839* (2013.01); *A61B 8/0833* (2013.01); *A61M 5/16854* (2013.01); *A61M 5/427* (2013.01); *A61M 5/46* (2013.01); *A61M 25/0693* (2013.01);

(Continued)

(58) Field of Classification Search
CPC ...................................... A61B 5/021
USPC ...................................... 600/481; 604/168.01
See application file for complete search history.

(56) References Cited

U.S. PATENT DOCUMENTS

| | | | | |
|---|---|---|---|---|
| 4,027,669 A | * | 6/1977 | Johnston | A61M 5/347 604/110 |
| 4,386,606 A | * | 6/1983 | Tretinyak | A61M 5/31501 604/220 |

(Continued)

FOREIGN PATENT DOCUMENTS

| | | |
|---|---|---|
| EP | 0 538 259 A1 | 4/1993 |
| EP | 0538259 A1 | 4/1993 |

(Continued)

OTHER PUBLICATIONS

Seldinger, Catheter Replacement of the Needle in Percutaneous Arteriography, Presentation at the NAMR, Helsinki, pp. 368-376 (Year: 1952).*

(Continued)

*Primary Examiner* — Patricia Mallari
*Assistant Examiner* — Tho Q Tran
(74) *Attorney, Agent, or Firm* — Fitch, Even, Tabin & Flannery, LLP

(57) ABSTRACT

Methods and devices for detecting positioning of a probe in a tissue of a patient. A method can include providing a detection device; advancing a device coupled probe through the tissue of the patient and toward the patient's target tissue; detecting a change in pressure about the distal portion of the coupled probe during advancing, where the detected pressure change indicates probe positioning in a vein or artery of the patient; outputting the detected pressure change or indication of probe positioning to a visual display.

22 Claims, 13 Drawing Sheets

(51) Int. Cl.
*A61B 8/08* (2006.01)
*A61M 5/168* (2006.01)
*A61M 5/46* (2006.01)
*A61B 17/34* (2006.01)
*A61B 8/00* (2006.01)

(52) U.S. Cl.
CPC ......... *A61B 8/4472* (2013.01); *A61B 17/3401* (2013.01); *A61B 2090/064* (2016.02)

(56) References Cited

U.S. PATENT DOCUMENTS

| | | | |
|---|---|---|---|
| 4,648,406 A | | 3/1987 | Miller |
| 4,801,293 A | | 1/1989 | Jackson |
| 5,125,898 A | * | 6/1992 | Kaufhold, Jr. ...... A61M 5/3234 604/110 |
| 5,171,299 A | * | 12/1992 | Heitzmann ........ A61M 25/1018 604/100.03 |
| 5,205,828 A | | 4/1993 | Kedem |
| 5,267,971 A | * | 12/1993 | Brimhall ........................ 604/177 |
| 5,314,410 A | * | 5/1994 | Marks ........................ 604/168.01 |
| 5,526,820 A | * | 6/1996 | Khoury ................ A61B 5/0215 600/561 |
| 5,575,789 A | | 11/1996 | Bell et al. |
| 5,711,302 A | | 1/1998 | Lampropoulos et al. |
| 5,865,764 A | | 2/1999 | Moorhead |
| 5,871,470 A | | 2/1999 | McWha |
| 5,902,273 A | | 5/1999 | Yang et al. |
| 5,954,701 A | | 9/1999 | Matalon |
| 6,165,142 A | * | 12/2000 | Bar ................ 600/595 |
| 6,623,429 B2 | | 9/2003 | Percival et al. |
| 7,274,956 B2 | * | 9/2007 | Mott .................... A61B 5/0215 439/304 |
| 7,585,280 B2 | | 9/2009 | Wilson et al. |
| 7,618,409 B2 | | 11/2009 | Hochman |
| 7,896,833 B2 | | 3/2011 | Hochman |
| 7,922,689 B2 | | 4/2011 | Lechner |
| 7,955,301 B1 | | 6/2011 | McKay |
| 8,142,365 B2 | | 3/2012 | Miller |
| 8,282,565 B2 | | 10/2012 | Mahapatra et al. |
| 8,328,738 B2 | | 12/2012 | Frankhouser et al. |
| 8,814,807 B2 | | 8/2014 | Hulvershorn et al. |
| 8,926,525 B2 | | 1/2015 | Hulvershorn et al. |
| 2002/0010390 A1 | | 1/2002 | Guice et al. |
| 2002/0035332 A1 | | 3/2002 | Chen et al. |
| 2003/0199909 A1 | | 10/2003 | Boecker et al. |
| 2004/0010204 A1 | | 1/2004 | Weber et al. |
| 2004/0024358 A1 | | 2/2004 | Meythaler et al. |
| 2004/0098020 A1 | | 5/2004 | Nardeo |
| 2004/0215080 A1 | | 10/2004 | Lechner |
| 2005/0070458 A1 | | 3/2005 | John |
| 2005/0148940 A1 | | 7/2005 | Miller |
| 2006/0009737 A1 | | 1/2006 | Whitling et al. |
| 2006/0036164 A1 | | 2/2006 | Wilson et al. |
| 2006/0122555 A1 | | 6/2006 | Hochman |
| 2006/0135882 A1 | | 6/2006 | Bleich |
| 2006/0149161 A1 | | 7/2006 | Wilson et al. |
| 2006/0195043 A1 | | 8/2006 | Rutherford et al. |
| 2007/0038129 A1 | | 2/2007 | Kishimoto et al. |
| 2007/0123888 A1 | | 5/2007 | Bleich et al. |
| 2007/0255220 A1 | | 11/2007 | King et al. |
| 2007/0265550 A1 | * | 11/2007 | Choi .................... A61M 5/427 600/584 |
| 2008/0097287 A1 | | 4/2008 | Nelson et al. |
| 2008/0147094 A1 | | 6/2008 | Bittenson |
| 2008/0154188 A1 | | 6/2008 | Hochman |
| 2008/0200789 A1 | * | 8/2008 | Brister ............... A61B 5/14542 600/347 |
| 2009/0005675 A1 | * | 1/2009 | Grunwald et al. ........... 600/424 |
| 2009/0005703 A1 | | 1/2009 | Fasciano |
| 2009/0131832 A1 | | 5/2009 | Sacristan Rock et al. |
| 2009/0157044 A1 | | 6/2009 | Liyanagama et al. |
| 2009/0204119 A1 | | 8/2009 | Bleich et al. |
| 2009/0240205 A1 | | 9/2009 | Wen |
| 2009/0270759 A1 | | 10/2009 | Wilson et al. |
| 2010/0069851 A1 | | 3/2010 | Vad et al. |
| 2010/0094143 A1 | * | 4/2010 | Mahapatra ........... A61B 5/4887 600/486 |
| 2011/0004159 A1 | | 1/2011 | Nelson et al. |
| 2011/0046477 A1 | | 2/2011 | Hulvershorn et al. |
| 2011/0054353 A1 | | 3/2011 | Hulvershorn et al. |
| 2011/0060229 A1 | | 3/2011 | Hulvershorn et al. |
| 2011/0125107 A1 | | 5/2011 | Slocum et al. |
| 2011/0130758 A9 | | 6/2011 | Bleich et al. |
| 2011/0224623 A1 | | 9/2011 | Velez Rivera |
| 2011/0298628 A1 | | 12/2011 | Vad et al. |

FOREIGN PATENT DOCUMENTS

| | | | | |
|---|---|---|---|---|
| FR | 2650957 A | * | 2/1991 | ............ A61M 25/00 |
| FR | 2650957 A1 | * | 11/1997 | ........ A61M 25/0014 |
| JP | S56104801 | | 8/1981 | |
| JP | H0686823 A | | 3/1994 | |
| KR | 2002-0073824 A | | 9/2002 | |
| WO | WO 93/09837 A1 | | 5/1993 | |
| WO | WO 03/000146 A1 | | 1/2003 | |
| WO | WO 2009/023247 A1 | | 2/2009 | |

OTHER PUBLICATIONS

U.S. Appl. No. 14/523,046, filed Oct. 24, 2014, Hulvershorn et al.
U.S. Appl. No. 14/268,975, filed May 2, 2014, Hulvershorn et al.
U.S. Appl. No. 14/322,015, filed Jul. 2, 2014, Hulvershorn et al.
Don, et al. A Study of Correlation between Epidural and CSF Pressure. The Journal of Korean Society of Anesthesiologists: vol. 23, No. 2, 1990.
European search report and opinion dated Mar. 6, 2014 for EP Application No. 10810289.8.
International search report and written opinion dated Oct. 15, 2010 for PCT/US2010/002305.
Notice of allowance dated Mar. 28, 2014 for U.S. Appl. No. 12/806,809.
Notice of allowance dated May 23, 2014 for U.S. Appl. No. 12/806,747.
Office action dated Jan. 9, 2014 for U.S. Appl. No. 12/806,747.
Office action dated Jan. 23, 2013 for U.S. Appl. No. 12/806,747.
Office action dated Mar. 8, 2013 for U.S. Appl. No. 12/806,809.
Office action dated May 7, 2013 for U.S. Appl. No. 12/806,798.
Office action dated May 17, 2013 for U.S. Appl. No. 12/806,747.
Office action dated Jun. 7, 2012 for U.S. Appl. No. 12/806,747.
Office action dated Sep. 6, 2013 for U.S. Appl. No. 12/806,809.
Office action dated Nov. 6, 2013 for U.S. Appl. No. 12/806,798.
Office action dated Nov. 19, 2012 for U.S. Appl. No. 12/806,798.
Usubiaga, et al. Effect of Saline Injections on Epidural and Subarachnoid Space Pressures and Relation to Postspinal Anesthesia Headache. Anesthesia and Analgesia Current Researches vol. 46, No. 3, May-Jun. 1976, 293-296.

* cited by examiner

VASCULAR ACCESS METHODS AND DEVICES

CROSS-REFERENCE TO RELATED APPLICATION

The present invention claims the benefit of priority under 35 U.S.C. § 119(e) of U.S. Provisional Application No. 61/235,004, filed Aug. 19, 2009 and U.S. Provisional Application No. 61/300,794, filed Feb. 2, 2010, the entire contents of which are incorporated herein by reference.

The present application is related to U.S. application Ser. No. 12/806,809, filed Aug. 19, 2010, and U.S. application Ser. No. 12/806,747, filed Aug. 19, 2010, both of which are being filed concurrently herewith, the full disclosures of which are incorporated herein by reference.

BACKGROUND OF THE INVENTION

The present disclosure relates generally to systems, methods, and devices for facilitating access to a target anatomical site. More specifically, methods and structures are provided for detecting and facilitating positioning of a probe in a vascular tissue of a patient, such as a patient's vein for central line or catheter placement.

Needles and catheters are routinely inserted or injected into a patient's body for various purposes or indications. One type of indication that involves such insertion is the placement of vascular lines or catheters, for instance, the placement of a central venous catheter (CVC). A CVC is typically used to administer fluids (e.g., intravenous (IV) drugs, chemotherapeutic agents, blood, or saline) into the body in medical situations in which large fluid transfer volume and/or high fluid transfer rate is desired. Common CVC insertion targets include an internal jugular vein, located in the neck; a subclavian vein, located in the chest; or a femoral vein, located in the groin.

During a central line procedure, a large tube (cannula) called a catheter is inserted into a central vein, like the internal jugular vein in the neck or the subclavian vein under the collarbone. Large arteries, like the carotid artery, lie next to these veins, and putting the catheter into the artery by accident (arterial cannulation) can result in serious injury, stroke or even death. In the event that a large bore catheter is accidentally inserted into an artery, emergency surgery is usually required to remove the catheter and repair the artery. To avoid arterial cannulation, the Seldinger technique was developed where a small introducer needle is used to locate the vein, before inserting the much larger catheter. The small needle can be safely removed from an artery or a vein—it only makes a small hole that is able to seal after the needle is removed. In this technique, a small introducer needle is attached to a syringe and the needle is inserted into the vessel. Blood is pulled back (aspirated) through the needle and into the syringe, and the color of the blood in the syringe is used to determine whether the introducer needle is an artery or a vein. Arterial blood is usually bright red and venous blood is darker. However, in sick patients this is not always true—arterial blood could appear quite dark in a patient with low blood oxygen levels.

Once the physician confirms that the needle is in the vein using the color of the blood, the syringe is removed and the blood is allowed to flow directly out the rear of the needle. If the blood "spurts" out the back of the needle, it is an indication that the needle might be in an artery. If the blood comes out of the needle slowly, the needle is likely in a vein. Unfortunately, there are many reasons why arterial blood might not "spurt" out of the needle, and so this method for identifying an artery is also prone to error. After looking at the blood color and pulsatility, if the physician decides that the needle is in a vein, a small flexible guidewire is inserted through the needle. The introducer needle is then removed and the catheter is inserted over the guidewire. The guidewire ensures that the catheter enters the vein.

A problem with CVC placement via the Seldinger technique alone is that misplacement of either or both of the needle and the CVC is still far too common. For example, an unintended puncture or tear of a venous wall and/or the placement of one or both of the needle and the CVC into an artery (i.e., an unintended arterial cannulation) can occur, which may result in serious and expensive complications including severe bleeding, emergency vascular surgery, stroke, and possibly death. Moreover, the Seldinger technique, which relies on both blood color and pulsatility to differentiate a vein from and artery, does not always prevent accidental arterial cannulation, and this error happens in as many as 1 out of every 100 procedures.

Manometry is a technique that has been used for verifying that an appropriate type of blood vessel has been targeted during catheterization (e.g., in association with the Seldinger technique). See, e.g., FIGS. 2A-F. Conventional manometry directed toward vascular target verification includes an extension set (e.g., a 50 centimeter extension tube set) attached to a needle or a catheter (e.g., an 18-gauge needle or catheter) that has been inserted into a vessel. Blood flows or is drawn from the patient's body into the needle or catheter, and further flows into an elevated section of tube along the extension set, thereby forming a blood column indicative of probe positioning (e.g., column height, color, pulsatility). The height attained by the blood column, e.g., gives an indication as to the pressure of the blood within the vessel under consideration. Such an assessment can enable the practitioner to verify a venous or an arterial placement of the needle or the catheter. However, needle or catheter occlusion or patient state or condition can impact the visible properties of the blood column, and hence the surgeon's assessment, which can lead to a false conclusion about needle or catheter placement. For instance, in a hypotensive patient, an inadvertent arterial needle insertion may not be readily apparent from a naked-eye assessment of blood column height within the elevated section of tube.

Once the physician decides that the needle is in a vein using this blood column, he detaches the tubing from the needle and then proceeds to insert the guidewire through the needle, leaving a "blind spot" where monitoring for needle positioning does not occur. A risk with this technique is that the needle can move while attaching or detaching the tubing; it is possible the needle could move from a vein to an artery after the tubing has been removed. If this were to happen, the tube based pressure measurement would not prevent arterial cannulation. Further, widespread adoption of manometry has been severely limited by procedure awkwardness, additional time, equipment and steps required, and the increased chance of infection. Studies show that many physicians do not routinely utilize manometry for verifying needle or catheter placement for at least some of these reasons. Accordingly, manometry procedures are generally cumbersome and not routinely used, and even when used the risk of complication (e.g., accidental arterial puncture or cannulation, infection, etc.) has not been eliminated.

Ultrasound has been conventionally utilized for determining the position of objects within the body, and can be utilized for facilitating placement or positioning of needles, guidewires, and catheters. See, e.g., FIGS. 3A-D. Reduced expense and increased portability of ultrasound equipment has led to application of ultrasound imaging to guide central line placement. However, one aspect of ultrasound guidance particularly relevant to discussion of arterial cannulation, is that the needle and/or wire may not always be visualized in the target vein. Because of the tomographic nature of an ultrasound beam, it is sometimes difficult to distinguish a needle shaft from the needle tip. Thus, confusion between the tip and the shaft of the needle in an image can lead to inadvertent arterial cannulation when the needle passes through the target vein and into a nearby artery. Further, recent surveys show that widespread use of ultrasound equipment in vascular catheterization procedures is limited to a small minority of practitioners (e.g., as little as 15%). The relative expense, lack of accessibility, equipment sharing between multiple groups or departments, and need for additional medical personal may explain the limited use of ultrasound in central line placement. Additionally, ultrasound guidance is not particularly well suited to guide catheters inserted into the subclavian vein (the most common access vein used in trauma situations). The subclavian vein is beneath the collarbone, and the collarbone blocks the ultrasound signal. Further, ultrasound ties up one hand, forcing the physician to perform the procedure with a single hand. For this reason, a second person is often used to assist during ultrasound guided procedures.

Accordingly, improved methods and structures are needed for facilitating probe access and/or positioning in a target vascular tissue, and could significantly improve efficiency and reduce complications associated with many medical procedures, such as central line or catheter placement in a vein of a patient.

BRIEF SUMMARY OF THE INVENTION

The present disclosure relates generally to systems, methods, and devices for facilitating access to a target anatomical site. More specifically, aspects of the present disclosure relate to methods and structures for detecting or facilitating positioning of a probe (e.g. a needle) in a vascular tissue (e.g., vein, artery) of a patient, including probe positioning, monitoring and the like during medical procedures such as venous catheter placement (e.g., central line procedure).

In one aspect, the present invention provides methods and structures for positioning, detecting or monitoring a probe for disposal in a vein or artery of a patient, such as a target vein (e.g., jugular vein, subclavian vein, femoral vein, etc.). A method can include providing a detection device as described herein. The device can be advanced distally such that the tip or a distal portion of a coupled probe (e.g., needle probe attached to a port of the detection device) advances through the tissue of the patient and toward the target site or vein of the patient. The method further includes detecting a change in pressure about the distal portion of the coupled probe during advancing, where the detected pressure change indicates probe positioning in the target site, vein or artery. The detected pressure change and indication of probe positioning is output, for example, as a reporting signal to the visual display. The user may change or alter advancement of the probe in response to the detected pressure change.

In an embodiment, a detection device includes a housing having a generally proximal portion and a distal portion, the distal portion may be coupled to a probe (e.g. a needle) during use. A device further includes a pressure sensing system at least partially carried by the housing and an output unit carried by the housing. The pressure sensing system includes a processor or processing unit coupled with a pressure sensor so as to receive signal from the pressure sensor and determine a pressure value of an environment about a distal portion of the coupled probe. The output unit is coupled to the pressure sensing system so as to receive a pressure value signal and output to the visual display a reporting signal indicating the determined pressure value and/or positioning of the probe in the tissue of the patient.

Devices and methods include monitoring or detecting positioning of a probe following initial positioning in a target site or vein, including in conjunction with placement of a guidewire and/or catheter. In one embodiment, a device can include an integrated guidewire port or port carried by the housing and configured to facilitate placement of a guidewire in the target vein via entry through the device housing. In use, probe positioning in a target vein is confirmed, followed by introduction of a guidewire into the port disposed on the housing. The guidewire is further advanced through a portion of the housing and out the device coupled probe disposed in the patient's vein. Pressure detection or monitoring can be accomplished during or after guidewire positioning as described. A catheter can also be introduced over the positioned guidewire.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION OF THE INVENTION

Figure 1:
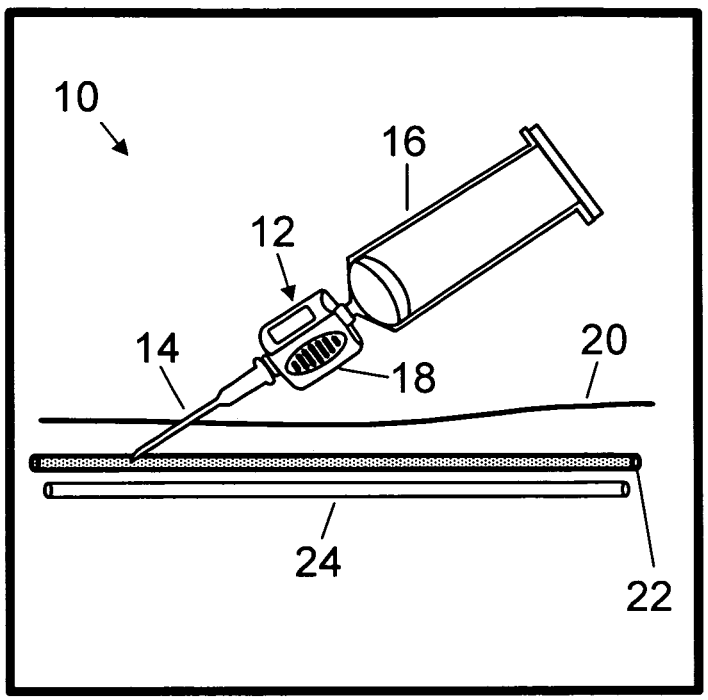
FIGS. 1A and 1B illustrate vascular access and guidewire positioning according to an embodiment of the present invention.
FIG. 1C is a diagrammatic view illustrating general anatomical features of a patient relevant to a vascular access procedure according to certain embodiments of the present invention.
Figure 1:
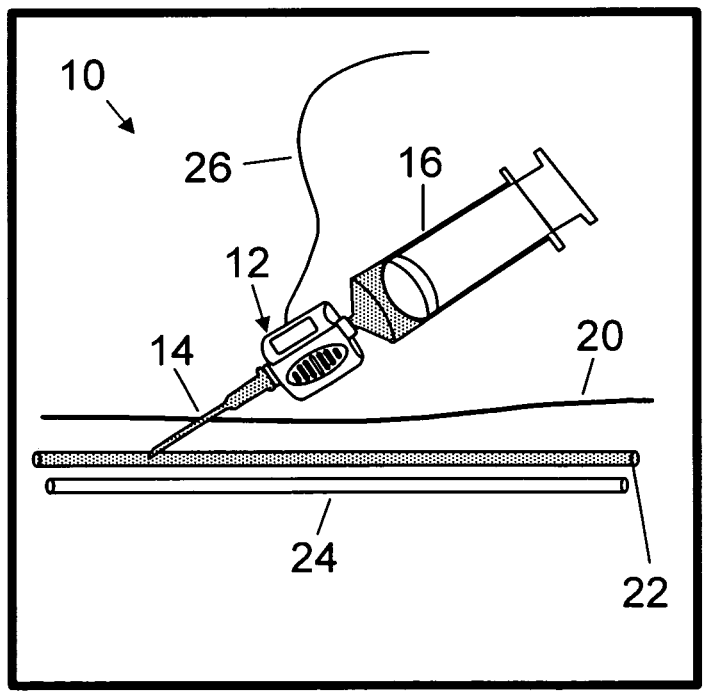

The present invention provides methods and structures for detecting and/or facilitating positioning of a probe in a vascular tissue of a patient. For instance, methods can include distinguishing between probe positioning in a vein or an artery, or facilitating venous access, e.g., during procedures such as venous catheterization or central line placement where it can be important to place a needle or catheter into a target vein or intravenous site, and generally avoid arterial or non-vascular placement.

A detection device according to an embodiment of the present invention will generally include a pressure detection system and display (e.g., housing integrated display) that allows users or medical practitioners to use pressure to differentiate a vein from non-vein tissue, such as an artery. The device can also allow continuous, non-continuous, or repeated pressure monitoring, such as during guidewire insertion, to confirm venous access throughout one or more stages of a procedure (e.g., central line procedure). As discussed further herein, the device can include an in-line configuration where components of the device (e.g., needle, housing, syringe) are assembled substantially in an axial arrangement, enabling convenient and in some cases simultaneous visualization of the needle, the patient, and the display during use. The device and methods of use can integrate with the way the physician would normally perform the procedure, thereby increasing likelihood of use among practitioners compared to other more cumbersome techniques. Devices can be provided as sterile and disposable, and can be used in the sterile field without presenting a contamination risk.

In use, a device can be inserted between a probe or introducer needle and syringe (see further discussion herein). The needle is then inserted into the patient's tissue and advanced toward the target tissue or blood vessel. As the needle enters the vessel, the device outputs a pressure reading to the user, which can occur rapidly and even before blood is channeled through the device and into the syringe for color visualization. The rapid or substantially "instant" pressure reading allows the physician to rapidly detect, for example, if the needle is an artery or a vein. With rapid pressure reading and reporting, the device can rapidly indicate when the needle is in a vessel, and prevent the user or physician from continuing to move or advance the needle in the patient's tissue, such as advancing the needle distally so as to exit the rear of the vessel (an undesirable occurrence known as a "through and through" because the needle enters one side of the vessel and then leaves the opposite side of the vessel).

Different display options or configurations for a detection device will be available, and may be selected at least partially based on intended use of the device. In an embodiment, a device display outputs or provides the user two different types of pressure readings, a numerical output and a non-numerical (e.g., graphical) output, which can include complementary but different readings or information. In a numerical output or reading, pressure can be detected, processed and output as an average pressure reading over a selected time. A numerical output or reading can be monitored by the user for indication of needle positioning, such as positioning in an artery or a vein. Because the pressure reading is an average, it also better represents a clinically relevant parameter, such as the central venous pressure in a vein or mean arterial pressure (MAP) in an artery. If the needle is not in a blood vessel, the numerical display does not display the average pressure, but instead may be programmed to update more frequently, which may help the user more easily or rapidly recognize tissue transitions that are accompanied by pressure changes. For example, if the needle is in tissue, the pressure may display a low pressure reading, such as approximately 0 mm Hg. Upon the needle leaving the tissue and entering a vein, the pressure will increase, such as jumping from about 0 mm Hg to about 10 mm Hg.

In addition to the numerical readout, the display can also include one or more non-numerical outputs, such as a 2-D graphical waveform or various types of non-numerical alerts, signals, or graphics. The device can be configured such that the waveform graph updates rapidly and so as to emphasize or illustrate the physiologic pulsations in the arteries and veins. For instance, the pressure in a vein goes up and down with the heartbeat and with breathing. Arteries have a large pressure fluctuation from the heartbeat. The device can be configured so as to output or display a graphical waveform scaled to illustrate either or both these small and large pressure fluctuations. A visual representation of the pressure fluctuations gives physicians an added confirmation that the pressures are coming from a vein or an artery. The absence of pressure fluctuations might indicate that the needle is not in a vessel.

Thus, a device may be configured to display one, two, or two or more outputs or pressure value displays, such as a numerical output and a non-numerical (e.g., graphical) output. In such an embodiment, the device may be configured such that two different pressure displays represent pressure values detected over different time periods or collection times, and/or different collection frequencies or averaging calculations. For example, a first pressure output might be a numerical output representing pressure measured over a first time period or collection time, or a given number of pressure readings obtained at a selected frequency. The same device may be configured with a second pressure output or reading, such as a graphical output, representing pressure measured over a second time period or a period where a selected number of pressure readings are obtained at a frequency. Output of two or more different pressure readings or displays can in some cases advantageously provide more useful or informative output to the user than a single pressure output/display.

In addition to providing pressure measurements and output for identification of needle positioning, e.g., in an artery or vein, a device can also include an integrated port for guidewire insertion. In certain embodiments including a guidewire port, a device may include a channel within the device that allows the guidewire to pass through the device (e.g., entry through the device housing) and distally out the needle. Device construction will be selected such that guidewire positioning does not substantially interfere with pressure detection functionality of the device. Further, the guidewire port can act as a substantially air-tight and/or fluid-tight (e.g., blood-tight) seal while still allowing the guidewire to pass through it with a minimum or resistance, permitting tactile feel introduction of the guidewire into the vessel. The seal is air-tight and water-tight before the guidewire is inserted, while the guidewire is passed through the seal, and again after the guidewire is removed from the seal. The pressure readings are accurate during all of these conditions.

Figure 2:
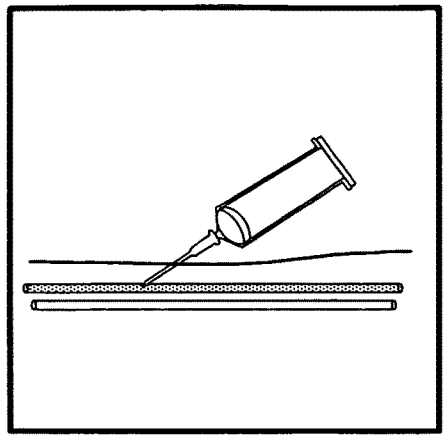
FIGS. 2A-F illustrate probe positioning under pressure manometry guidance.
Figure 2:
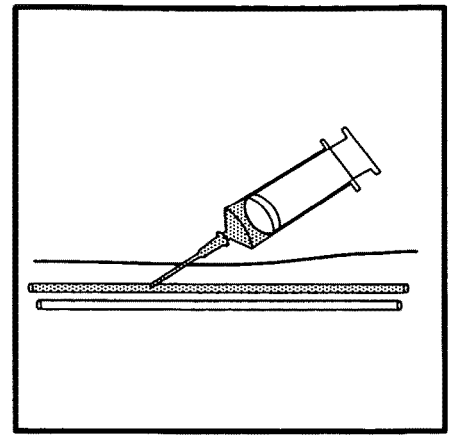
Figure 2:
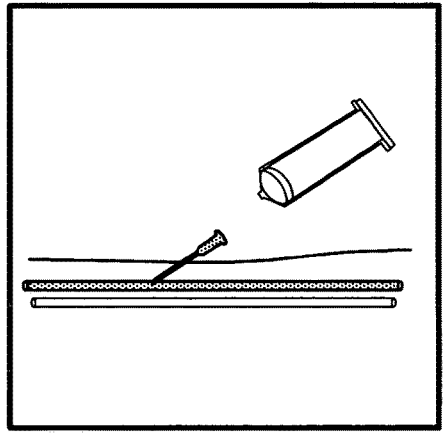
Figure 2:
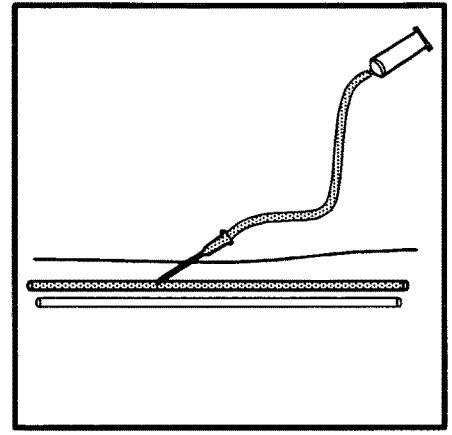
Figure 2:
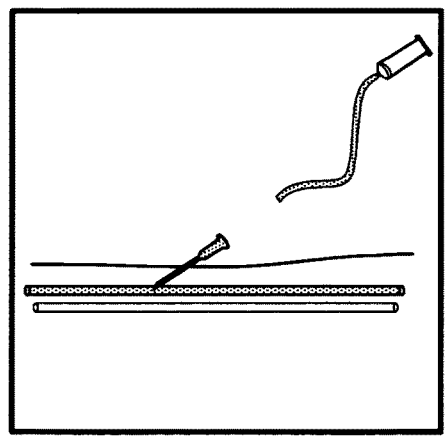
Figure 2:
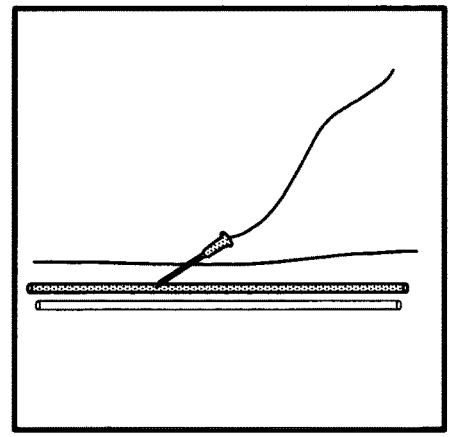

Thus, in use of a device with an integrated guidewire port, such a port can allow a user to insert the guidewire through a positioned needle and into a blood vessel with reduced manipulation of the device or access equipment. For example, guidewire positioning may be accomplished without necessarily requiring detachment of a syringe from the device or detachment of the device from the positioned needle. Such reduced manipulation can advantageously reduce risk of error due to unwanted needle movement, such as dislodging the needle from the vein. Further, use of an integrated guidewire port can allow the user to verify or monitor pressure during and/or after insertion of the guidewire into the vein. This is in contrast to previous methods to measure pressure or positioning, which may indicate venous access prior to inserting the guidewire, but present a "blind spot" at least during the insertion of the guidewire when the pressure is not measured (see, e.g., FIGS. 2-3).

Following insertion of the catheter, the device can also be utilized to verify and/or monitor correct catheter placement. For example, the device may be coupled to the catheter and pressure detected via the catheter, detecting or verifying whether the catheter is inserted in a vein or artery.

Guidewire placement according to a method of the present invention using a device with an integrated guidewire apparatus is illustrated with reference to FIGS. 1A and 1B. As shown, an assembly 10 is utilized including a detection device 12 having a distally coupled needle 14 and a proximally coupled syringe 16. The detection device 12 further includes a guidewire port or apparatus carried by or integrated with a portion of the device 18 housing. In use, the coupled needle is entered through the patient's tissue and toward the target tissue or blood vessel. Tissue pressure is detected by the device 12 and output to a display for indication of needle positioning (e.g., vein, artery, non-vascular tissue) and viewing of pressure readings by a user. FIG. 1A illustrates a patient's tissue including non-vascular tissue 20, a first blood vessel, e.g., a vein 22, and a second blood vessel, e.g., an artery 24, with the distal portion of the needle 14 positioned in a vein of the patient. As noted, pressure readings output to the display of the device will be indicative of needle location (e.g., vein, artery, etc.). The user may additionally pull back the syringe to draw blood and visualize blood and color, for further indication of needle positioning. With the needle 14 positioned in the vein 22, a guidewire 26 can be introduced into the device 12 and into the needle, as illustrated in FIG. 1B. The guidewire 26 can advance distally out the needle 14 and/or the needle removed or withdrawn from the vein 22 with the guidewire 26 remaining at least partially disposed in the vein 22. Pressure detection or monitoring with the device 12 can occur throughout the procedure. Further, guidewire placement can be accomplished while limiting or eliminating removal and/or exchanging of assembly components.

Figure 1C:
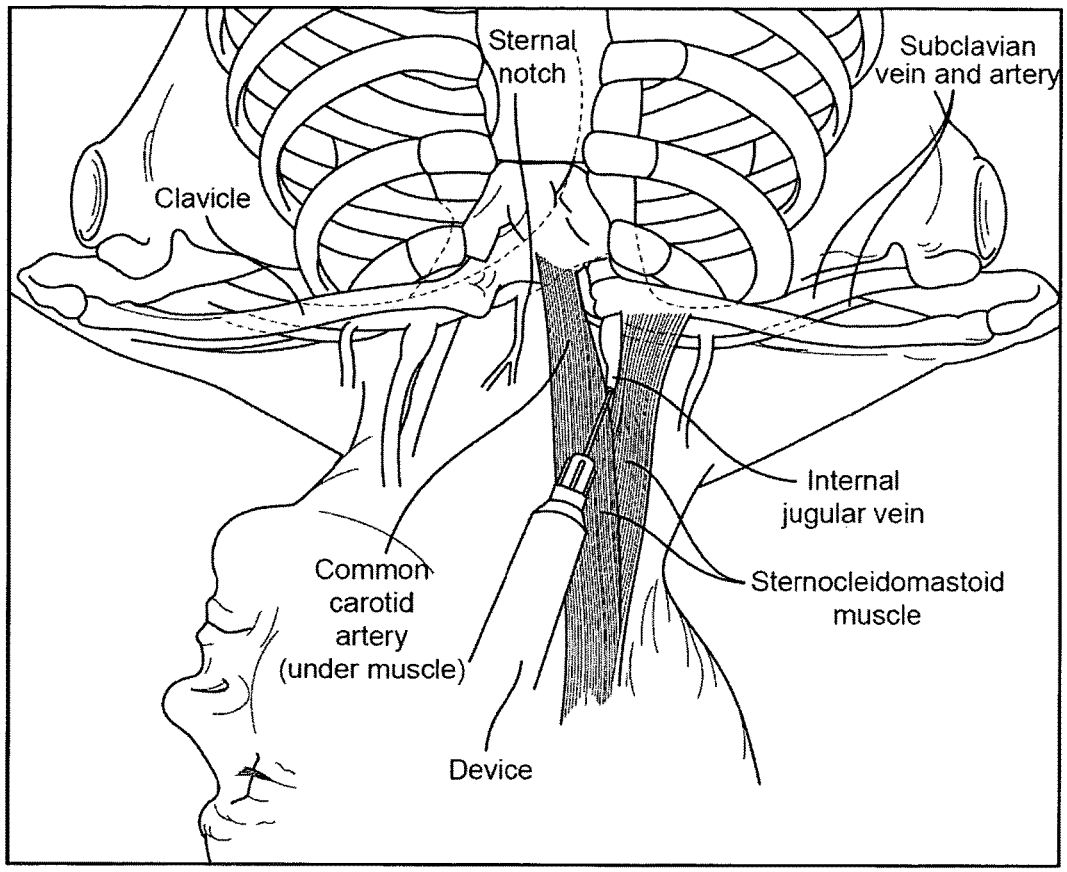

FIG. 1C illustrates general anatomical features of a patient relevant to a vascular access procedure or central line placement according to certain embodiments of the present invention. In central line placement, access and entry to the subclavian vein or internal jugular vein is commonly of interest. FIG. 1C illustrates a device with coupled probe positioned in the internal jugular vein of the patient, as one example of venous access. As shown, the subclavian vein bears close proximity to the subclavian artery, while the internal jugular vein lies near the subclavian artery low in the neck, as well as near the carotid artery throughout its course in the neck. With such close proximity of target access veins to arterial vessels, a certain degree of precision is required in central line placement procedures. The positioning of tissues such as the clavicle adds further difficulty to venous access as the clavicle can block or complicate use of imaging techniques, such as ultrasound guidance. Methods and devices of the present invention include pressure monitoring and detection for venous access or central line placement in the illustrated anatomical environment, as well as other anatomical sites or target tissues (e.g. the femoral vein).

Figure 3:
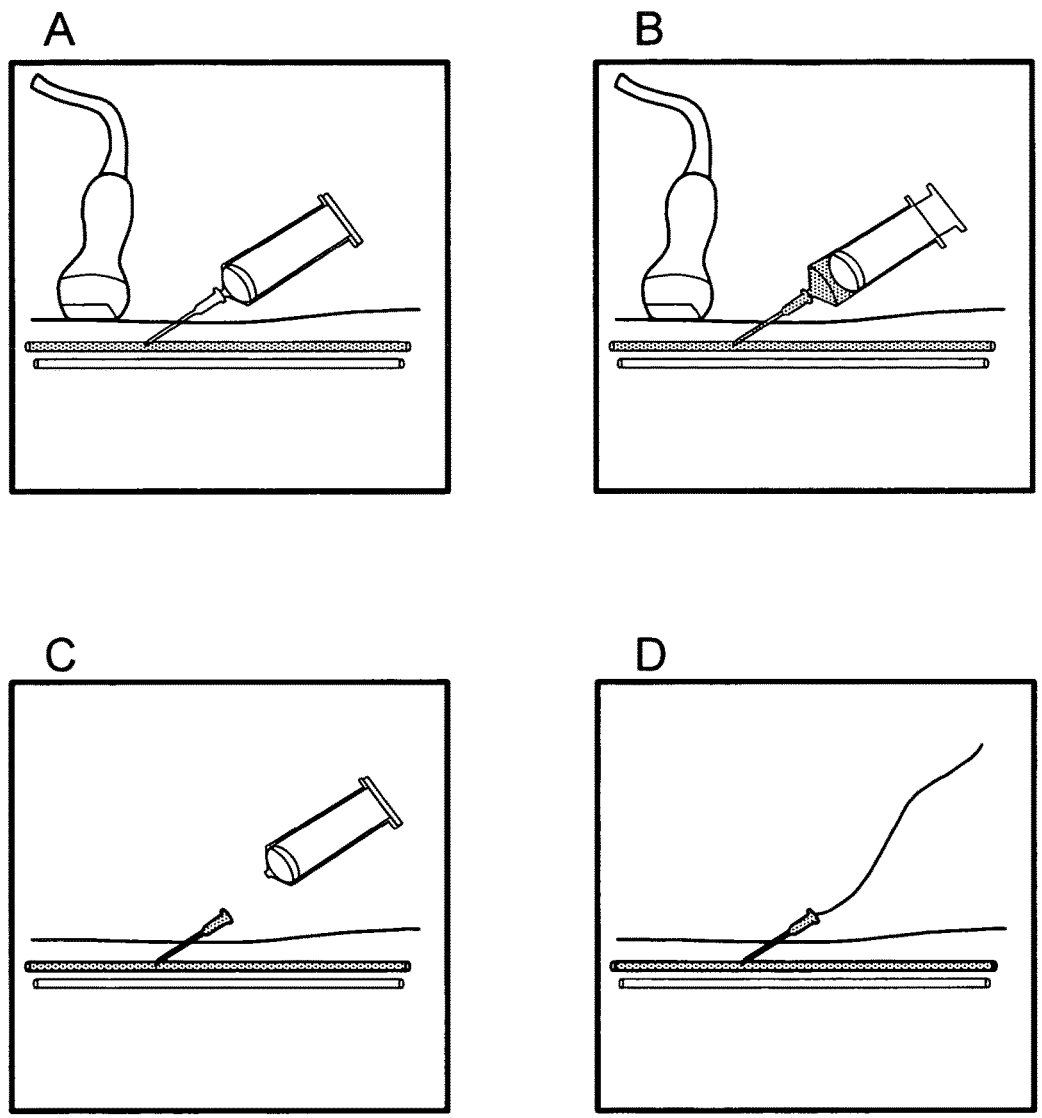
FIGS. 3A-D illustrate probe positioning under ultrasound guidance.

Embodiments including a device with an integrated port for introducing a guidewire may advantageously permit a user to introduce a guidewire into a target location or lumen while limiting additional component exchanging steps and/or undesired probe movement. Such simplification of the guidewire placement procedure can help minimize occurrence of error or patient injury due to probe misplacement, as illustrated with reference to FIGS. 1A and 1B above, and with further reference to FIGS. 2-3. FIGS. 2A through 2F illustrate probe tip location indication under pressure measurement (e.g. column manometry) guidance. Such pressure measurement guidance includes "blind spot" component exchanging (e.g., FIGS. 2E and 2F) where no positioning monitoring occurs and that can cause undesired movement of the probe and potential patient injury. FIGS. 3A through 3D illustrate probe tip location detection under ultrasound guidance, with FIGS. 3C and 3D illustrating "blind spot" needle positioning and component exchange steps that may elicit undesired movement of the probe positioned in the tissue and potential injury to the patient, similar to column manometry above.

Different types of objects or probes, for example, needles, catheters, tubes, and devices can be inserted into a subject's body for various medical purposes or indications. Accurate placement or positioning of such objects within the body is generally required. For instance, during certain vascular access procedures such as certain central line placements, it is important to place a needle, as well as guidewire and catheter into the vascular space to perform the given procedure, e.g., the jugular vein or subclavian vein.

Embodiments of the present disclosure are directed to systems, devices, apparatuses, methods, and processes for facilitating, indicating, and/or verifying access to at least one type of target or intended anatomical environment, substance, site, location, structure, tissue, organ, cavity, and/or lumen. Particular embodiments are further directed to systems, devices, apparatus, methods, and processes for indicating or verifying access to at least one type of non-target, unintended, or inadvisable anatomical environment (e.g., in view of a medical procedure directed to the target anatomical environment). Embodiments of the present disclosure can include or involve systems, devices, apparatuses, methods, or processes for detecting, sensing, capturing, measuring, and/or analyzing one or more substances or signals associated with particular physiologic parameters or conditions to facilitate the identification, evaluation, or verification of a location of a portion of an object within a body (e.g., relative to a target or intended anatomical site).

Several embodiments of the disclosure are directed to categorizing or distinguishing between aspects of one or more anatomical substances or sites, for instance, to differentiate or indicate a difference between a first or target anatomical site and a site other than a target anatomical site (e.g., a second or non-target anatomical site); or to determine or indicate whether an anatomical substance originates from or was supplied by, extracted from, or acquired at a first or target anatomical location or structure or a second or non-target anatomical location or structure. Such embodiments can facilitate an automatic or semi-automatic verification or notification that a portion of an object inserted into a body has transitioned into, resides at or within, or has transitioned away from a target substance or site, or one or more non-target substances or sites. Particular embodiments of the disclosure are directed to distinguishing between a blood vessel (e.g., vein, artery) and non-blood vessel tissue, as well as between different types of blood vessels, such as between a vein and an artery.

The presence, absence, relative or absolute level, or change in a physiological parameter (e.g., pressure) can directly or indirectly correspond to an anatomical location or environment at which a portion of the probe resides, and/or a patient state or condition. The system or apparatus may optionally additionally include a processing unit configured to a) generate physiologic parameter values using signals output by the set of sensors; and b) analyze or evaluate particular physiologic parameter values. The system or apparatus further includes an output unit configured to generate at least one type of feedback (e.g., audio and/or visual feedback) that indicates whether a portion of the probe under consideration is exposed to or resides at a first or target anatomical site or substance, or a second or non-target anatomical site or substance. In various embodiments, each of the processing unit and the output unit can be carried by the housing, which can be a single use or disposable structure (e.g., a disposable cartridge).

Representative aspects of embodiments of systems, apparatuses, devices, and processes of the present invention are described in detail hereafter with reference to the identified figures. The description herein provides for embodiments that are suitable for indicating successful or unsuccessful venous puncture or access, or guidewire or catheter placement (e.g., central line placement) and the like; and embodiments suitable for other medical indications.

Figure 4:
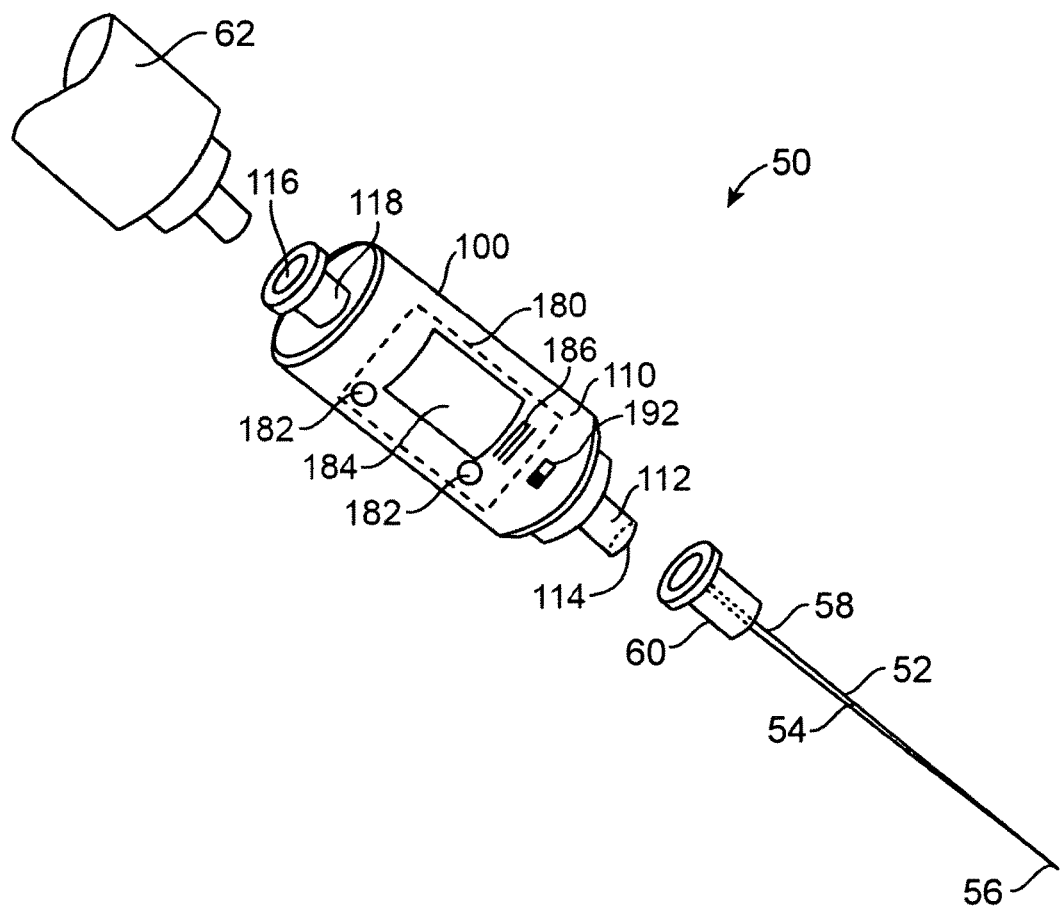
FIG. 4 is a perspective illustration of an apparatus according to an embodiment of the disclosure.

FIG. 4 is a perspective illustration of an apparatus 50 for indicating a probe or probe tip location or environment according to an embodiment of the disclosure. In an embodiment, the apparatus 50 includes a probe site indication device (PSID), probe tip location device (PTLD), or anatomical environment characterization device (AECD) 100 (hereafter "device" or "detection device") that is coupled to a probe such as a needle 52. The needle 52 includes an elongate member or shaft 54 having a first or insertion end or distal tip 56 and a second or proximal end 58. The needle's shaft is hollow, that is, the needle's elongate member includes a bore that extends between the needle's tip 56 and its proximal end 58. The needle's proximal end 58 can be coupled to a conventional needle coupling or fitting structure 60, such as a Luer adapter, connector, sleeve, collar, or lock. In certain embodiments, the apparatus 50 can further include a syringe 62 that can be coupled to the detection device 100, for instance, by way of a conventional syringe coupling or fitting such as a Luer adapter, connector, sleeve, collar, or lock.

Figure 5:
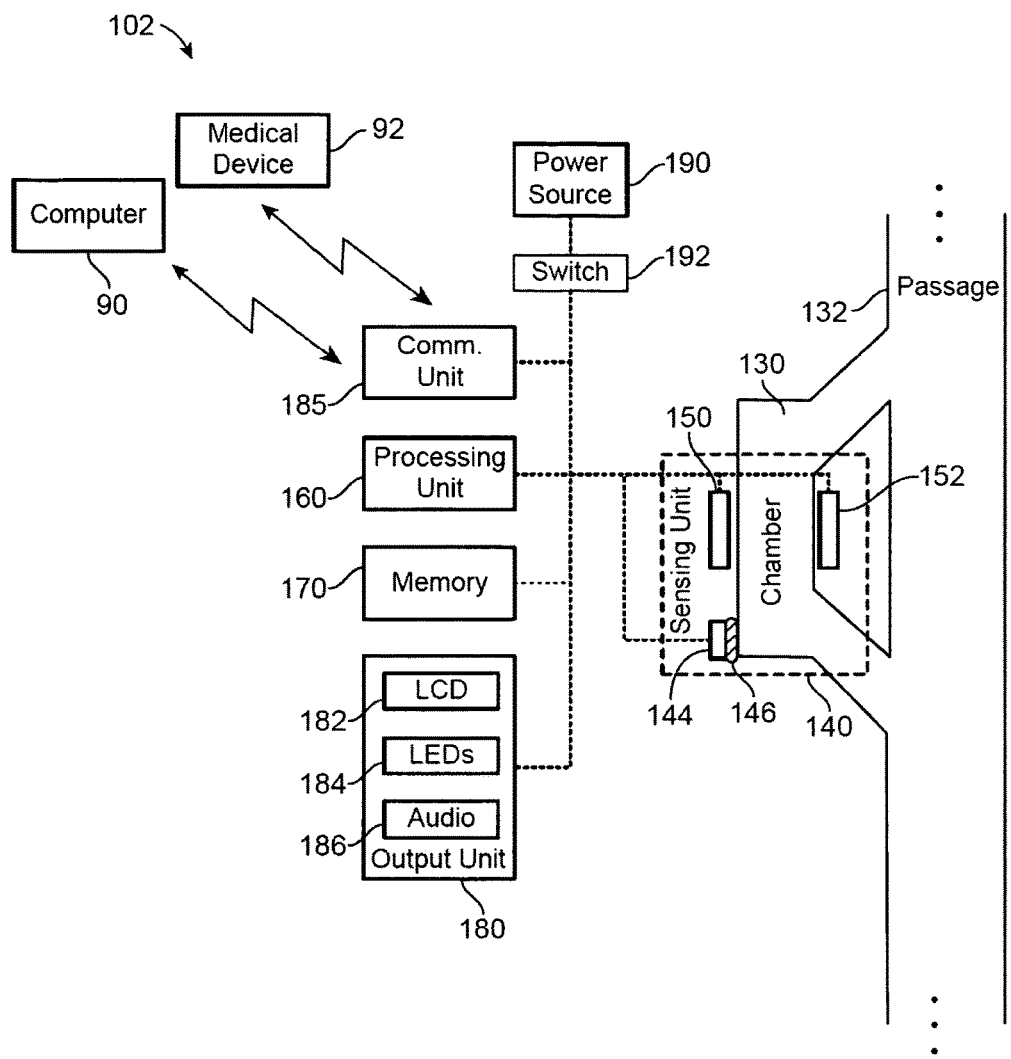
FIG. 5 is a block diagram of a system according to embodiment of the present invention.

FIG. 5 is a block diagram of a detection device 100 according to an embodiment of the disclosure. With simultaneous reference to FIG. 4, in various embodiments the detection device 100 includes a housing 110 that carries a first coupling structure 112, a first opening or port 114, at least one fluid or substance detection or analysis chamber or corridor 130 (e.g., a flow-through chamber 130), a sensing unit 140, a processing unit 160, a memory 170, an output unit 180, a power source 190, and an activation switch 192. In some embodiments, the housing 110 can additionally carry a passage 132, a second opening or port 116, and a second coupling structure 118. Each of the sensing unit 140, the processing unit 160, the memory 170, and the output unit 180 are coupled to the power source 190 by way of the switch 192. Selection of a predetermined switch position or a switch toggle can activate the detection device 100. In an embodiment, the power source 190 includes a battery or a capacitor configured to power the detection device 100 for a predetermined or expected total amount of time (e.g., at least a few minutes to a few hours, approximately 2 hours, approximately 12 hours, approximately 1 day, or another amount of time).

The first coupling structure 112 carries the first port 114, and includes one or more coupling, fitting, securing, retaining, or connecting elements configured to mate with a given type of probe or needle 52. Similarly, the second coupling structure 118 carries the second port 116, and includes one or more coupling, fitting, securing, retaining, or connecting elements configured to mate with another medical implement such as the syringe 62. One or both of the first and second coupling structures 112, 118 can include or be, for instance, a Luer adapter, taper, collar, slip, connector, or lock structure. For instance, the first coupling structure 112 can include a male Luer lock fitting, and the second coupling structure 118 can include a female Luer lock fitting. In an embodiment, the first and second coupling structures 112, 118 are carried at opposite sides or ends of the housing 110. Each of the first and second coupling structures 112, 118 can carry a removable or pierceable/penetrable end cap or seal (not shown) to facilitate the maintenance of a controlled environment within the device 100.

In an embodiment, the chamber 130 includes or forms a cavity or compartment into which a fluid or substance can flow or be drawn, and the passage 132 includes or forms a channel or bore through which the fluid or substance can flow or be drawn. The chamber 130 and the passage 132 are fluid communicable or in fluid communication with the bore of the needle 52 by way of the first port 114. The passage 132 extends between the first port 114 and the second port 116, and hence the second port 116 is fluid communicable or in fluid communication with the bore of the needle 52 by way of the passage 132. Upon insertion or injection of the needle 52 into an individual's body, a bodily fluid such as blood can flow or be drawn from the tip 56 of the needle into the chamber 130 and the passage 132. The bodily fluid can further flow or be drawn through the passage 132 into the syringe 62.

The sensing unit 140 includes a set of sensors, sensing devices, or sensing elements in sensing communication with the chamber 130. More particularly, the sensing unit 140 is in signal and/or substance communication with the chamber 130, such that the set of sensing elements can directly or indirectly apply signals to a substance within the chamber, detect or measure particular properties of a substance present within the chamber, and/or subject a substance within the chamber to one or more tests. Particular sensing elements may detect, measure, or test a property of a substance within the chamber in a manner that avoids direct contact with the substance, while other sensing elements may detect, measure, or test a property of a substance within the chamber by way of direct access to or physical contact with the substance. The chamber 130 can include one or more openings, windows, or ports to facilitate direct access to or physical contact with a substance carried within the chamber 130.

Particular sensors or sensing devices generate sensing signals that correspond to one or more physiologic properties of a substance within the chamber 130 at a particular time. Depending upon the nature or characteristics of a given set of sensing signals, the set of sensing signals may directly provide a value or measure of a physiologic parameter, or the set of sensing signals may be a correlate or partial correlate of the physiologic parameter. If a set of sensing signals provides one or more physiologic parameter correlates or partial correlates, a number of mathematical operations can be applied to at least a subset of signals within the set of sensing signals to generate, determine, or estimate at least one physiologic parameter value.

Any given sensing device operates in accordance with a sensing device modality, which corresponds to a type of signal that the sensing device is configured to acquire and/or a type of physiologic measurement that can be generated or obtained using the sensing signal. A particular sensing device can operate in accordance with a modality such as pressure sensing, optical sensing, temperature sensing, fluid dynamics sensing, chemical or biological species sensing, or another modality. Depending upon embodiment details, the set of sensors or sensing devices can include one or more light emitting diodes (LEDs), semiconductor lasers, optical detectors (e.g., photodiodes, which can be configured to detect optical signal characteristics such as intensity, peak wavelength, or phase shift), pressure sensors (e.g., a diaphragm and/or a pressure transducer such as a piezoelectric transducer), temperature sensors (e.g., an optical temperature sensor or a thermocouple), fluid flow sensors (e.g., a Doppler ultrasound transducer and detector), substance or environment sensing field effect transistors (e.g., a chemical sensing or chemically modified FET (ChemFET), an ion sensitive FET (ISFET), an Enzyme modified FET (EnFET), or an electrolyte-oxide-semiconductor FET (EOSFET)), an electrophoresis device, a biological microchip (e.g., a biochip) or a microfluidic lab-on-a-chip (e.g., as described by Rohit Pal et al. in "An integrated microfluidic device for influenza and other genetic analyses," *Lab on a Chip*, Royal Society of Chemistry 2005, 5, 1-9), and/or other sensing elements or devices.

In an embodiment, with respect to sensing pressure related parameters (e.g., for a catheter or central line placement procedure), the set of sensing elements can include a pressure sensor or pressure sensing system, e.g., such as a piezoelectric pressure transducer 144 coupled to a diaphragm 146 that is exposed to an opening in the chamber 130. When the chamber 130 is in communication (direct or indirect) with tissue or fluid source, anatomical pressure exerts a displacement force upon the diaphragm 146. The diaphragm 146 in turn exerts a force upon the piezoelectric pressure transducer 144, which generates an electrical signal corresponding to an instantaneous, quasi-instantaneous, or near-instantaneous pressure reading at a distal probe segment or the probe tip 56.

The sensing unit 140 is configured to output signals (e.g., sensing signals) to the processing unit 160 and/or the memory 170 on a continuous or periodic basis, and/or in response to one or more sensed parameter values exhibiting a change that exceeds a predetermined magnitude relative to one or more previously sensed parameter values. With respect to the above described embodiment directed to indicating pressure for vascular access and/or monitoring, the sensing unit 140 can store and/or output a series of instantaneous or near-instantaneous pressure values and/or a set of measured values in the memory 170.

The processing unit 160 can include a state machine, a microcontroller, a microprocessor, an application specific integrated circuit (ASIC), or a field programmable gate array (FPGA) or programmable logic device (PLD) configured to correspond to or execute program instruction sequences (e.g., software and/or firmware) directed to receiving, operating upon, evaluating, analyzing, interpreting, and/or transforming signals generated by one or more portions of the sensing unit 140, and determining whether the tip 56 of the needle 52 resides within a target anatomical site, structure, or substance. In an embodiment, particular program instruction sequences can additionally or alternatively be directed to determining whether the needle tip 56 resides within one or more non-target, undesirable, or inadvisable anatomical sites, structures, or substances. Furthermore, such program instruction sequences can be directed to determining whether the needle tip 56 has transitioned into, resides within, or has transitioned away from one or more intermediary tissues or anatomical environments along a needle insertion trajectory toward a target anatomical destination or environment. In certain embodiments, particular structural portions or operational aspects of the processing unit 160 can be included or incorporated within the sensing unit 140.

In an embodiment, a given type of sensing device operates in accordance with a particular sensing modality and generates a particular type of sensing signal, which depending upon sensing device or sensing signal type can directly or by way of mathematical correlation or transformation provide a physiologic parameter value and hence an indication of a probe tip position. The processing unit 160 can use or mathematically operate upon a set of sensing signals corresponding to a given type of sensing device to determine a single type of physiologic parameter value, or multiple distinct types of physiologic values that differ from each other by way of a set of mathematical operations. For instance, the processing unit 160 can generate a mean value of a physiologic parameter using a time series of sensing signals generated by a given type of sensing device. Additionally or alternatively, the processing unit 160 can additionally or alternatively generate a maximum or mean value of a physiologic parameter fluctuation, range, amplitude, or magnitude using this time series of sensing signals. The processing unit 160 may process received pressure value signal for recognition of a pressure profile or pattern, such as recognition of a pressure profile, reading(s), or range characteristic of a vein or artery. As a representative example, the processing unit 160 can average a series of sensed instantaneous vascular pressure values to determine a mean pressure value with respect to a predetermined time period (e.g., fraction of a second, approximately 1-10 seconds, 30 seconds, 1 minute, or longer). The processing unit 160 can additionally or alternatively determine a maximum and/or average pressure fluctuation value relative to a predetermined time period.

The memory 170 can include an electronically or computer programmable or readable medium having one or more of a Random Access Memory (RAM), a Read Only Memory (ROM) such as a type of programmable ROM (PROM), a set of registers, or other data storage elements for storing a) program instruction sequences; b) signals generated or output by the sensing unit 140 or physiologic parameter values corresponding thereto; and c) reference data that facilitates the determination, evaluation, or analysis of sensed physiologic parameter values. For instance, the memory 170 can store pressure data, pressure profile data, or a set of program instructions can access to facilitate the evaluation or analysis of sensed pressure values for identification or detection of vascular tissue (e.g., vein, artery) access (or lack of access) or positioning of a probe therein. The memory 170 can also store data (e.g., in a data structure such as a lookup table) that a program instruction sequence can access to a facilitate an assignment or mapping of a set of sensed physiologic parameter values to a categorization of the needle tip's location with respect a target, a non-target, and/or an intermediary anatomical structure or substance, as further detailed below. In association with the execution of one or more program instruction sequences, the processing unit 160 issues or transfers reporting signals to the output unit 180 to facilitate the provision of visual and/or auditory feedback corresponding to the needle's sensed location. In various embodiments, the reporting signals can indicate whether a needle portion such as the tip 24 resides at a first/target anatomical location (e.g., by way of a first set of reporting signals), or a second/non-target anatomical location (e.g., by way of a second set of reporting signals that are perceptually different than the first set of reporting signals), as further detailed below. In one embodiment, the reporting signals can further indicate whether the needle resides at neither a first/target anatomical location nor a second/non-target anatomical location (in which case the needle may reside at an anatomical location that is unrelated to the first/target anatomical location and the second/non-target anatomical location). Particular aspects of processes that can correspond to an automated sequence (e.g., performed by way of program instruction execution) directed to presenting physiologic parameter values to a user (e.g., a surgeon or other medical professional) or observer and/or indicating a position of a probe segment or tip 56 relative to a target, non-target, and/or intermediary anatomical site or structure are described further herein.

In response to the reporting signals, the output unit 180 is configured to generate and actively provide or convey visual and/or auditory signals that can indicate (e.g., in a selective manner) whether the needle resides at or within a target or non-target anatomical site, structure or substance. In an embodiment, the output unit 180 actively provides or conveys a visual and/or auditory indication of a needle location by applying a non-zero amount of power to an output device, thereby activating the output device to selectively emit, radiate, or externally propagate one or more signals/set of signals that provides a user or observer with sensory feedback (visual and/or auditory feedback) indicative of pressure of the environment in which the needle is disposed and/or needle location.

Depending upon embodiment details, the reporting signals can correspond to notification signals and/or alert signals. Notification signals can indicate or provide one or more detected, measured, or estimated physiological parameter values corresponding to sensing unit operation. Notification signals can include, for instance, visual and/or auditory signals corresponding to one or more physiologic parameter values such a pressure value, and/or a pulsatility measure or a peak-to-minimum pressure difference value. Alert signals can include visual and/or auditory signals that provide a binary or "yes/no" indication or a likelihood indication (e.g., a probability based indication, as determined in association with the execution of a program instruction sequence) of an intended or appropriate probe or needle positioning. In an embodiment, alert signals can further provide a binary or "yes/no" indication or a likelihood indication of an unintended, undesirable, or incorrect probe positioning.

The output unit 180 can output multiple reporting signals in a simultaneous or non-simultaneous (e.g., sequential) manner. Notification or alert signals can be presented on an essentially continuous, sampled, or periodic basis following detection device activation, or in response to a trigger event such as a first detection of one or more physiologic parameter values that correspond to a target or a non-target anatomical needle tip placement, or a predetermined change in a physiologic parameter value.

In general, the output unit 180 can include one or more types of output devices, for instance, a user interface or display (such as a liquid crystal display or LCD) 182, a set of LEDs 184, and possibly an audio device such as a speaker 186. In an embodiment, notification signals displayed by the display 182 (e.g., on a real-time, near real-time, a periodic basis, or in response to a given amount of physiologic parameter change) can include or correspond to particular physiologic parameter value(s). The presentation of particular physiologic parameter values to a user or observer can facilitate the determination or confirmation of a probe location. Signals output to the user via the output unit or components thereof (e.g., display) are not limited to any particular type and can include, e.g., pressure values (including any number of different measurement units for pressure), messages, text, graphs, pattern recognition alert, symbols, flashing lights, audio alters, and the like, as well as any combination of any number thereof.

According to another embodiment of the disclosure, the device 102 can optionally be configured to communicate with a remote or external device such as a computer system 90 (e.g., a desktop computer, a laptop computer, or a personal digital assistant) and/or a given piece of medical equipment 92. A communication unit 185 can optionally be coupled with the device, so as to configure a device, system, or assembly for wireless or wire-based signal transfer involving the device 102 and a remote computer system 90 and/or medical device 92, such as an ultrasound system or device (e.g., portable ultrasound unit), and the like.

Figure 6:
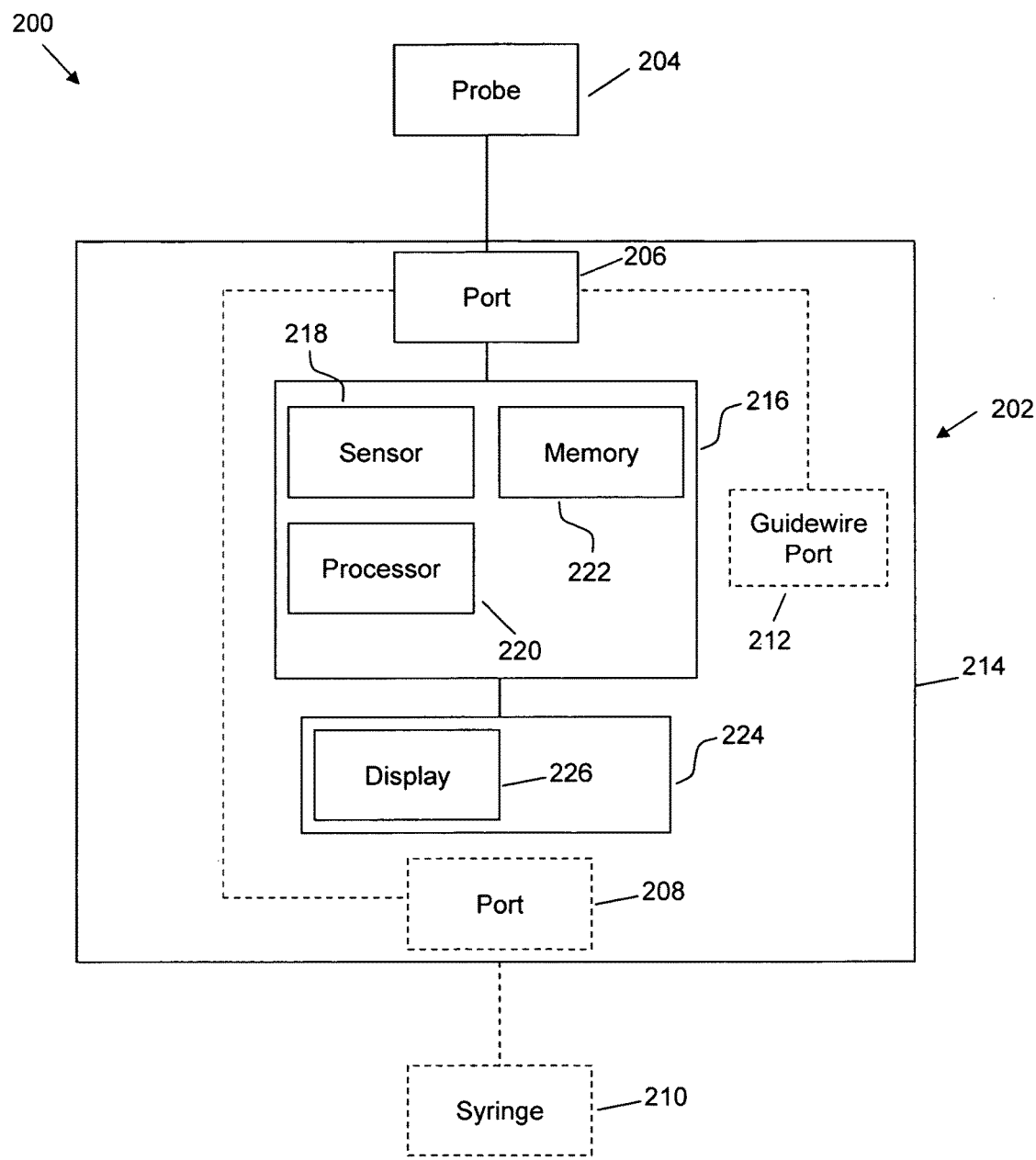
FIG. 6 is a block diagram of a system according to another embodiment of the present invention.

FIG. 6 is a block diagram illustrating a detection device system or assembly, including certain components thereof, according to an embodiment of the present invention. The assembly 200 includes a device 202 couplable to a probe 204 by a port 206. The device 202 further optionally includes a port 208 couplable to a syringe 210, and can further optionally include a guidewire introduction structure or port 212. The device 202 can include a housing 214 having a port 206 and port 208, which can generally be disposed on opposing sides or portions of the device so as to provide the general "in-line" assembly when the device is coupled together with a probe 204 and a syringe 210. In a pressure sensing embodiment, the device 202 further includes a pressure sensing system 216 that will be at least partially carried by the housing 214. The pressure sensing system 216 includes at least a pressure sensor 218 and corresponding electronics, as well as internal structure or configuration, necessary for detection of a pressure value in an environment (e.g., patient tissue, fluid, vessel, etc.) in which the probe 204 is at least partially disposed. The pressure sensing system 216 may also include electronics and/or components necessary for processing, output, and/or storage of detected pressure values/signals. For example, the pressure sensing system may include a processor 220 and/or memory 222. The pressure sensing system 216 further includes an output unit 224 that can include a graphical interface or display 226. The output unit 224 is at least partially carried by the housing 214 and coupled to the pressure sensing system 216 such that detected pressure values and corresponding signals can be output to the display for communication of pressure information to the user or device operator. The interface or display 226 can include a housing-integrated display that will be readily or easily visible to a device operator during use of the device. For example, the display may be carried on an upper or top side of the housing, or side opposite a portion of the housing designed for hand-held gripping by the user. The display 226 may also be disposed such that a surface of the display (e.g., viewing surface) is at an angle relative to a long axis of the device/assembly (see e.g., FIG. 9A). For example, the display 226 may be angled proximally for more optimized visualization by the user. The embodiment illustrated in FIG. 6 may, though not necessarily, further include any one or more of components, aspects, or features described further herein with regard to structures or methods of the present invention.

Figure 7:
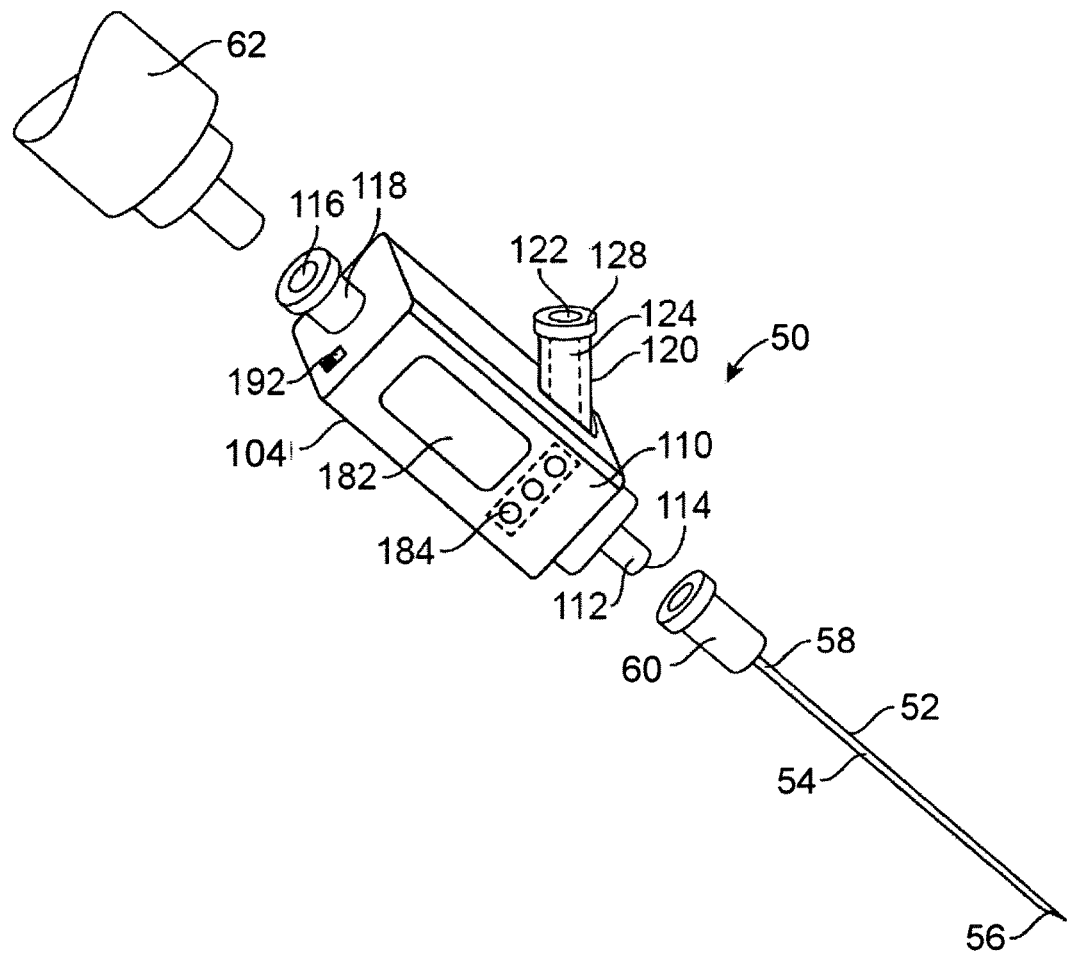
FIG. 7 illustrates an apparatus with an integrated port (guidewire port) according to another embodiment of the disclosure.

FIG. 7 is a perspective illustration of an apparatus 50 for indicating a probe segment or probe tip location according to another embodiment of the disclosure. In an embodiment, the apparatus includes a probe or needle 52 that is coupled to a detection device 104 having at least one auxiliary, adjunctive, subsidiary, or supplementary access structure, member, or shaft 120. The auxiliary access structure 120 includes an auxiliary access port 122 configured for fluid communication with the device passage 132. In an embodiment, the auxiliary access port 122 resides at a distal portion or end of a channel 124 carried by the auxiliary access structure 120. A proximal portion or end of the channel 124 is coupled to the passage 132 by way of an opening, such that the auxiliary access port 122 is fluid communicable or in fluid communication with the passage 132. The auxiliary access structure 120 can extend at a predetermined angle (e.g., approximately 45 degrees) away from a surface or side of the device 104. In general, the auxiliary access structure 120 is offset from a device surface or side that carries the output unit 180.

The auxiliary access port 122 facilitates the insertion of one or more types of auxiliary or adjunctive devices into the passage 132 of the device 104, and possibly through the device 104 and into or through the bore of the needle 52. An auxiliary device can include, for instance, a guidewire or a sensing device that carries a set of sensing elements configured for insertion into a patient's body. The auxiliary access structure 120 can carry a removable or pierceable/penetrable end cap or seal (not shown) that prevents the exposure of a fluid present within the device 104 to an external environment until the seal is removed or pierced. Additionally, the auxiliary access structure 120 can include a set of dynamic sealing elements 128 such as one or more o-rings (e.g., located or seated at a distal segment or end of the auxiliary access structure 120) that facilitate the maintenance of a leak proof or leak resistant seal around the periphery of an auxiliary access device after auxiliary access device insertion. The presence of a dynamic sealing element 128 can ensure that sensed blood pressure values remain accurate or consistent after an auxiliary access device such as a guidewire that resides within a portion of the device 104.

Depending upon embodiment details, the auxiliary access structure 120 can carry or include one or more types of structural elements that facilitate the maintenance of pressure integrity within the device 104 following insertion of a guidewire or other device (e.g., a set of optical fibers) into the auxiliary access port 122 and the auxiliary access structure's channel 124.

Relative to a physiologic parameter of interest (i.e., pressure), a given patient population can exhibit a range of physiologic parameter values, particularly when different patient subpopulations are considered, such as typical, normal, or healthy patients as well as less typical, abnormal, or health-impaired patients. For instance, exemplary physiologic pressure value ranges that might be relevant to a vascular access procedure are shown below with reference to Table 1.

Table 1 illustrates exemplary venous and arterial blood pressure ranges associated with patient states corresponding to low blood pressure conditions, normal blood pressure conditions, and high blood pressure conditions.

TABLE 1

Exemplary Venous and Arterial Pressure Conditions

| Vessel Type | Low Pressure | Normal Pressure | High Pressure |
|---|---|---|---|
| Vein | <5 mmHg | 5-25 mmHg | 25-40 mmHg |
| Artery | 45-55 mmHg | 55-160 mmHg | >160 mmHg |

Figure 8:
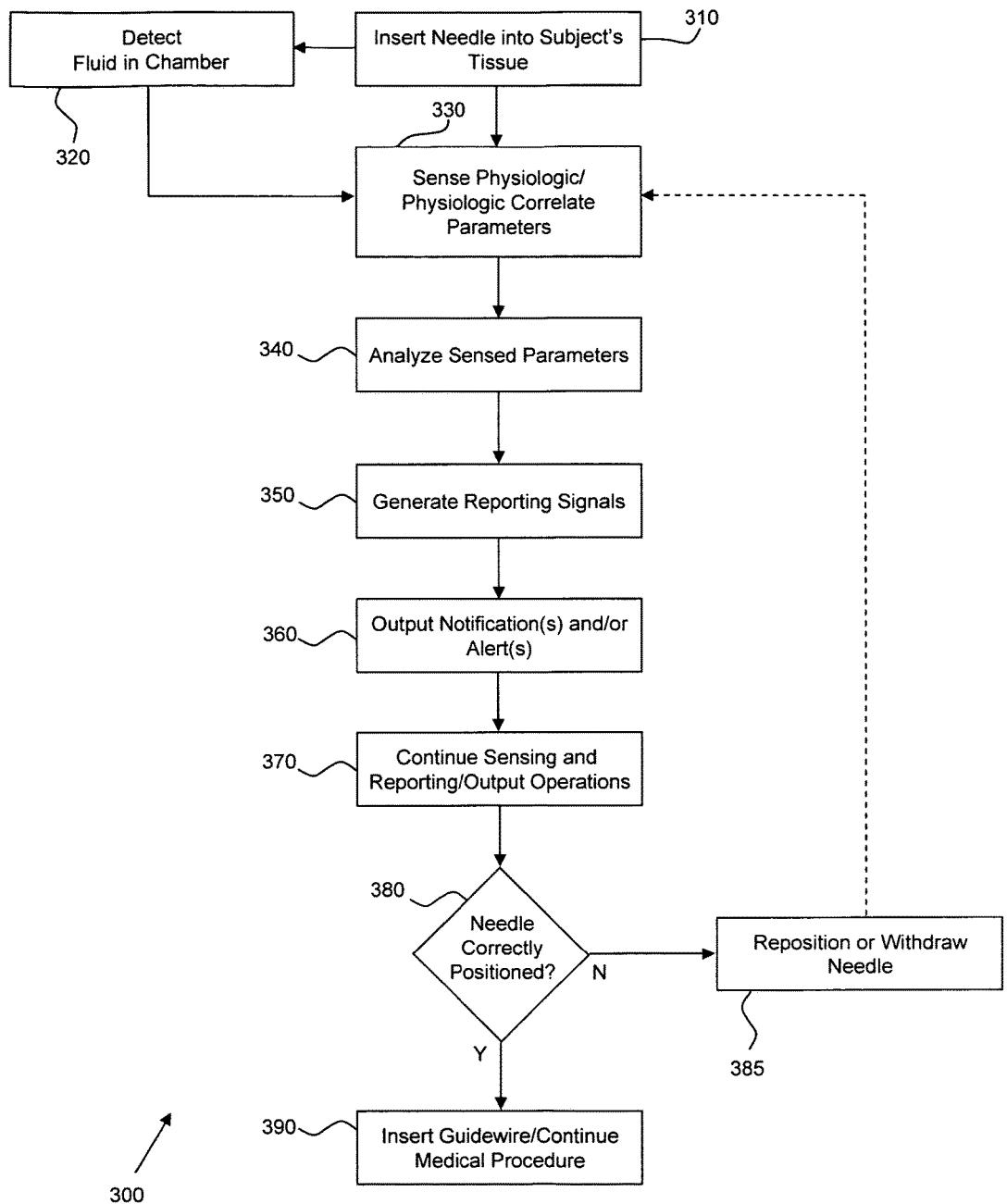
FIG. 8 is a flow diagram of a vascular access process according to an embodiment of the disclosure.

FIG. 8 is a flow diagram of a method or process 300 for indicating probe or needle tip positioning relative to a target vascular structure or substance according to an embodiment of the disclosure. Certain one or more steps or portions of the process 300 can be performed, for instance, by way of a processing unit's execution of program instructions and/or by user action. In an embodiment, the process 300 can include coupling a detection device to a probe or needle, and possibly coupling the device to a syringe. The process includes activating the device or receiving an activated device, and inserting the probe or needle into the patient's tissue (Step 310).

The process 300 may further include flowing a bodily substance or fluid (e.g., blood) within a device chamber, for instance, by the bodily fluid flowing or being drawn from the probe or needle tip through the bore of the probe or needle and into the chamber (Step 320). The process 300 also includes sensing or detecting a pressure parameter(s) corresponding to the fluid in the chamber, for instance, one or more of an instantaneous or average fluid pressure, or a fluid pressure variation or range.

The process 300 can further include characterizing, evaluating, or analyzing the set of sensed or measured physiologic parameter values corresponding to the fluid within the chamber (Step 330). For example, analyzing per Step 340 can include a transformation or conversion of particular sensed physiologic parameter correlate values to a measure or estimate of a value for a physiologic parameter. In another example, analysis can include a comparison of sensed or measured parameter values relative to one or more reference or threshold physiologic parameter values stored in a memory of a device to facilitate discrimination between venous and arterial blood, and hence discrimination between a probe or needle tip positioning within a vein or an artery. For instance, if the sensed or measured parameter values indicate an average pressure of less than approximately 40 mmHg and/or a pressure variation of less than approximately 15 mmHg, such readings may indicate that the probe or needle tip resides in a vein. If the sensed or measured parameter values indicate an average pressure of greater than approximately 45 mmHg and/or a pressure variation of greater than approximately 20 mmHg, indication may be that the probe or needle tip resides in an artery.

The process can further include generating or outputting reporting signals, e.g., to an output unit, where the reporting signals can correspond to or include notification and/or alert signals (Step 360), and can further include presentation of notification and/or alert signals using one or more output devices. Updated notification and/or alert signals can be presented on a continuous or periodic basis (Step 370), e.g., for determination of whether the probe or needle tip remains in a target or intended type of bodily tissue or fluid, or has moved into a non-target or unintended type of bodily tissue or fluid. Based on pressure sensing, detection, and/or output as described, a determination of whether the needle is correctly positioned can be made (Step 380), and further determination of whether to reposition or withdraw the needle (Step 385) or continue the procedure (Step 390) such as with guidewire and/or catheter insertion.

Figure 9A:
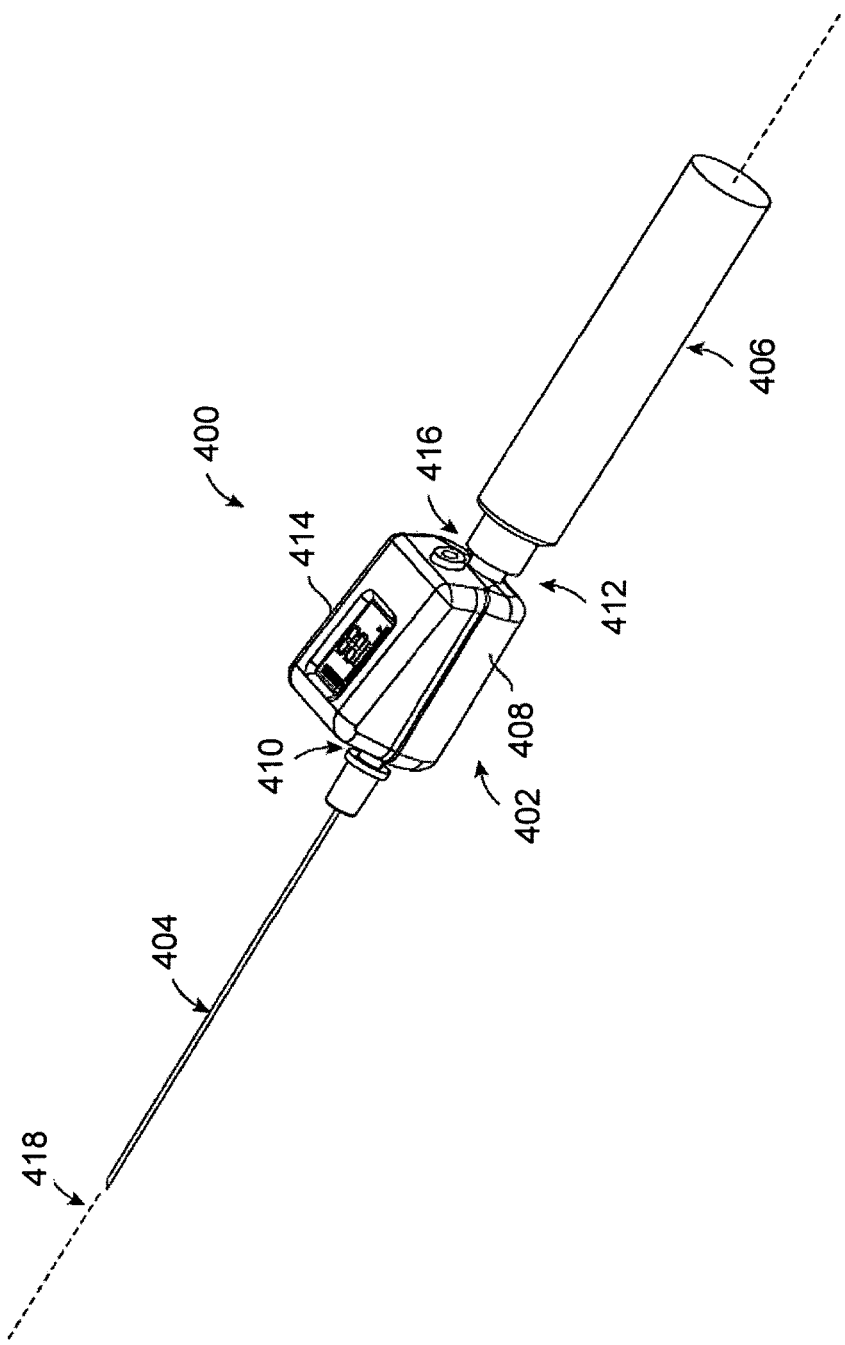
FIG. 9A illustrates an assembly including a detection device coupled to a probe and a syringe, according to another embodiment of the present invention.

FIG. 9A illustrates a detection device assembly, according to an embodiment of the present invention. The assembly 400 includes a detection device 402 coupled distally to a probe 404 and proximally to a syringe 406. The device 402 includes a housing 408 having a distal portion with a port 410 that is detachably coupled to a probe 404, and a proximal portion with port 412 that is detachably coupled to a syringe 406. Additional components, including those described above such as a sensing unit, processing unit, output unit, etc. (not shown), can be further carried by the housing 408. A housing of a device can include a single piece or multipiece assembly. The device 402 additionally includes a display 414 for reporting or visually displaying a determined biological parameter, such as a pressure value. The device 402 further includes a guidewire port 416 integrated with or carried by the housing 408.

A long axis 418 of the assembly is shown to illustrate an axial alignment or in-line assembly of components, including the probe 404 and syringe 406 coupled with the device 408. Components need not be limited to any particular positioning with respect to the long axis. But axial alignment or in-line assembly will generally refer to an ordered arrangement of certain components with respect to a long axis reference. In the embodiment illustrated in FIG. 9A, the assembly includes an in-line arrangement with the device 408 disposed substantially between the coupled probe 404 and the syringe 406. Referring to the device 402, certain components (e.g., sensing unit, processing unit, output unit, display, etc.) can be carried by the housing 408 so as to be disposed substantially between port 410 and port 412. The display 414 can be carried by the housing 408 such that the display 414 or surface thereof (e.g., outer surface) is at an angle with respect to the long axis 418 of the assembly 400. For example, the display can be angled proximately as illustrated. Such a configuration of the display may be selected so as to allow a user, viewing the display from a location generally proximal to the device, to more easily view the display during operation.

In use, a user can manipulate or control positioning of the assembly while grasping or holding the assembly about the device 402 and/or syringe 406. The distal portion of the probe 404 can be inserted into a tissue or body of a patient. With positioning, a biological parameter (e.g., pressure) of the environment in which the probe 404 is positioned is detected or determined, and the parameter value or information output for visualization on display 414. Device and assembly operation is further described elsewhere herein.

As described above, a device may be configured to display two or more outputs or pressure value displays, such as a numerical output and a non-numerical (e.g., graphical) output. In such an embodiment, the device may be configured such that two different pressure displays represent pressure values detected over different time periods or collection times, and/or different collection frequencies or averaging calculations. For example, a first pressure output might be a numerical output representing pressure measured over a first time period or collection time, or a given number of pressure readings obtained at a selected frequency. The same device may be configured with a second pressure output or reading, such as a graphical output, representing pressure measured over a second time period or a period where a selected number of pressure readings are obtained at a frequency. Output of two or more different pressure readings or displays can in some cases advantageously provide more useful or informative output to the user than a single pressure output/display.

Figure 9B:
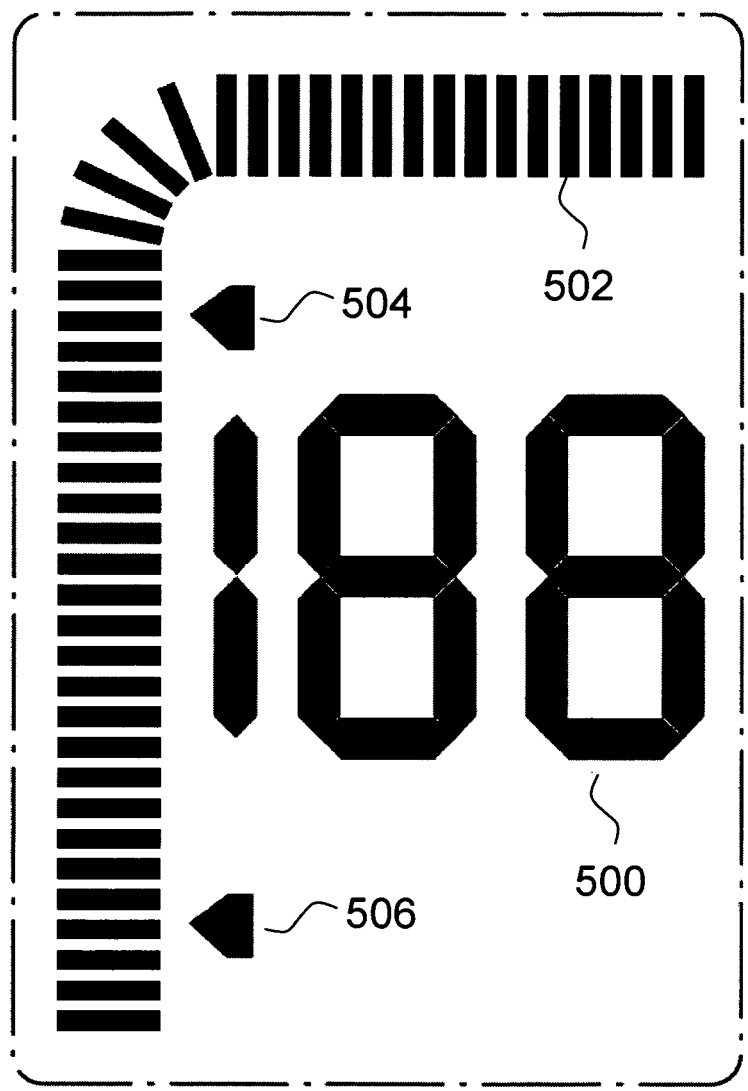
FIG. 9B illustrates an exemplary display, according to an embodiment of the present invention.

FIG. 9B illustrates a device display according to an exemplary embodiment of the present invention. The display presents at least two different pressure value displays: a numerical display 500 and a non-numerical display 502. The numerical display 500 can be selected to present a pressure value in a given unit of measurement, such as mmHg and the like. The non-numerical display 502 is illustrated as a bar-graph where the number of bars displayed is directly proportional to a pressure reading. The non-numerical display 502 can further include indicators 504, 506 that demarcate a relevant pressure range. Such a range may be selected to represent a target tissue expected pressure range, such that a reading within the range indicates probe positioning within the target tissue (e.g., vein). A reading below or above the range can indicate probe positioning outside the target area, such as in non-target, non-vascular tissue or in a non-target artery.

Figure 10:
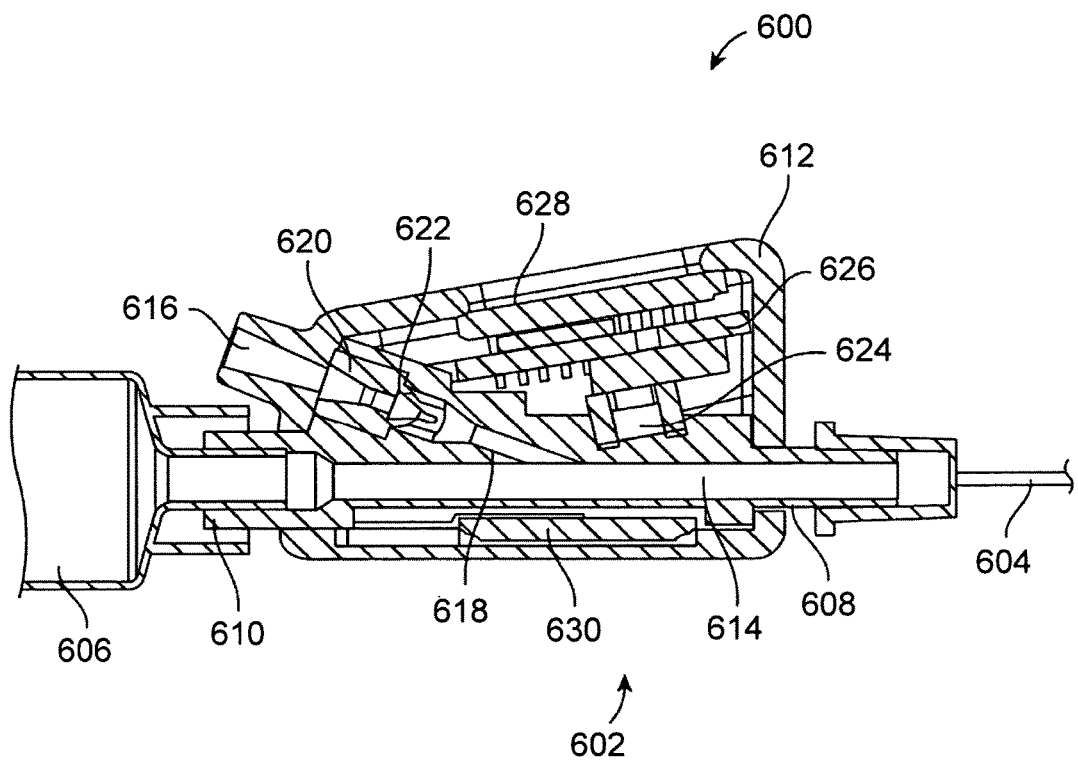
FIG. 10 is a diagram of an apparatus having an integrated guidewire port, according to another embodiment of the present invention.

FIG. 10 shows a diagram of an apparatus for indicating a probe segment or tip location, according to another embodiment of the present invention. The assembly 600 includes a device 602 with a probe 604 removably coupled to a distal portion of the device and a syringe 606 removably coupled to a proximal portion of the device. The probe 604 is coupled to the device about a port 608 carried by housing 612 including a distal male Luer fitting, and the syringe 606 is coupled to the device about a port 610 including a proximal female Luer fitting. Port 610 and port 608 are fluidly coupled about channel 614. Channel 614 and/or housing 612 may be at least partially transparent or translucent exteriorly to the device so as to allow visualization of a fluid within channel 614. The device 602 further includes guidewire port 616 fluidly connected to channel 614 about guidewire port channel 618. The guidewire port 616 is in assembly with seal cup 620 and seal 622 so as to provide a self-sealing assembly. The device further includes sensor 624 (e.g., pressure sensor) in operable communication with channel 614 so as to enable detection of a parameter (e.g., pressure) of an environment in which probe 604 is positioned. The device 602 further includes electronics and signal processing components 626 (e.g., similar to as described above), including a printed circuit board, processor, and the like, as well as power source 630. Display 628 is carried by the housing 612 and angled proximally with respect to a long axis of the assembly.

Figure 11:
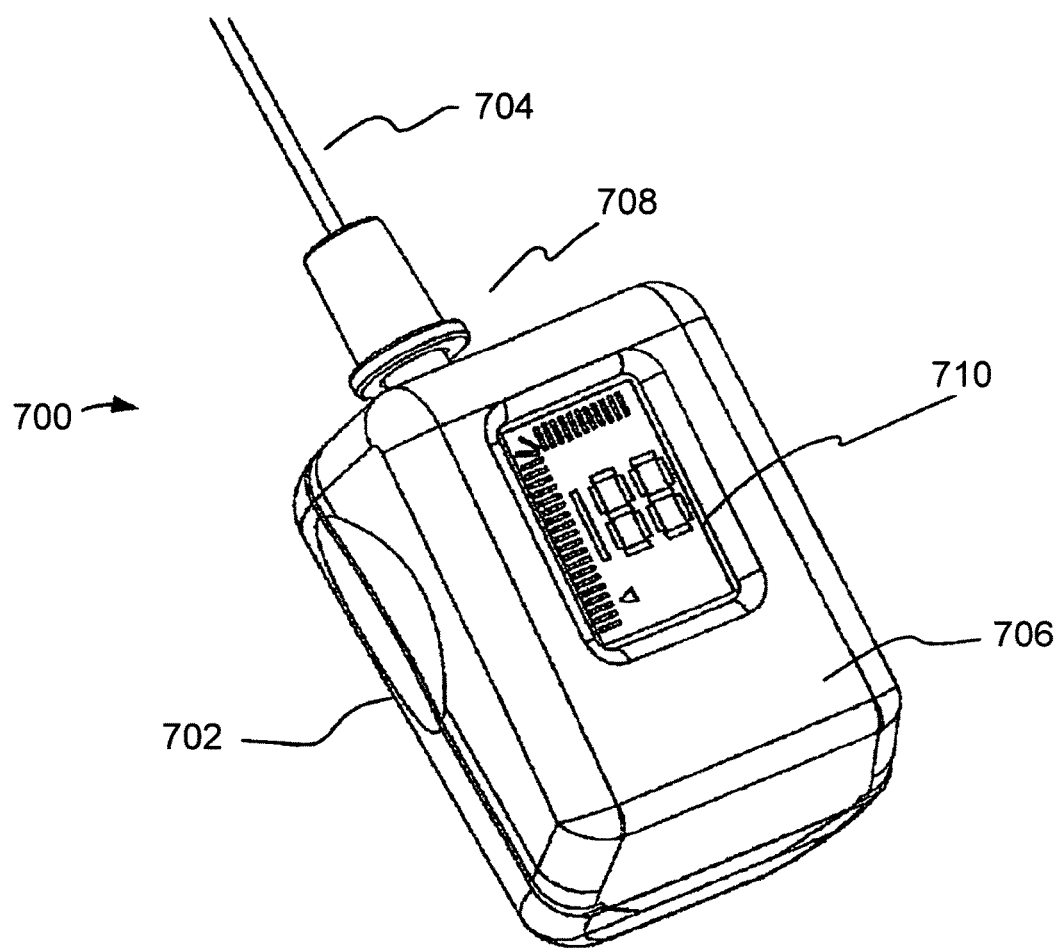
FIG. 11 illustrates an assembly including a detection device with a closed proximal portion and a distal portion coupled to a probe, according to an embodiment of the present invention.

In yet another embodiment, a device of the present invention can include a "closed" portion, such as a closed proximal portion lacking a port. FIG. 11 illustrates an assembly 700 including a detection device 702 coupled with a probe 704. The device 702 includes a housing 706 including a distal portion and a proximal portion. The distal portion of the housing includes a port 708 couplable to the probe 704. The proximal portion of the device 702 is closed in the sense that it lacks a port or opening. Additional components, including those described above such as a sensing unit, processing unit, output unit, etc. (not shown), can be further carried by the housing, with the housing of a device including a single piece or multipiece assembly. The assembly 700 includes an "in-line" configuration with respect to the coupled probe 704 and device 702, similar to as described above. The device 702 further includes a display 710 carried by the housing 706. The display 710 may be disposed on the housing 706 and angled proximally so as to allow more optimal viewing by a user during manipulation of the assembly 700, such as positioning a distal portion of the probe 704 in a tissue of a patient.

As described, in certain embodiments, a device of the present invention can include one or more guidewire access ports. In other embodiments, a device may be sans a separate guidewire port. In the case of the latter embodiments, a guidewire may still nonetheless optionally be utilized in conjunction with a device, such as in catheter placement. In one embodiment, a probe coupled to a device can be positioned in a target blood vessel and a guidewire may be entered through a syringe port, through the probe, and into the patient's blood vessel. In another example, following probe positioning, a device can be detached from the positioned probe and a guidewire entered through a proximal portion of the probe and into the patient's blood vessel. Objects other than a guidewire (e.g., catheter) can be positioned in a blood vessel of a patient as described herein.

In certain embodiments, indicated above, a device of the present invention can be coupled wirelessly to one or more graphical displays positioned remotely from the device, thereby enabling wireless monitoring of signal detection with the device. As an example, the detection device could have both a local display and also transmit data (e.g. pressure data) wirelessly to a remote monitor or device. As another example, the data from the detection device can be transmitted wirelessly to a storage unit, allowing storage and later retrieval of the data. Such storage and retrieval might be utilized, for example, for quality control, diagnostic, or research purposes. For example, the storage unit could save venous and/or arterial pressures, ranges, thresholds, and the like. A time stamp or the serial number of the particular pressure transducer could assist with identifying the data at a later time. Detection data can be collected and processed, and then utilized to update or reconfigure programming in new and/or existing devices, e.g., for improved performance.

A wireless system could also be used to change display monitors without the need to move additional hardware, such as bulky wires. For instance, a dongle or other type of wireless receiver could receive data from the device and convert the wireless signal to a standard electrical output signal (e.g. 5 V/mm Hg) to impute to a remote monitor. If a patient is transported, the dongle could be moved from a permanent monitor to a portable monitor for transport, and then plugged into a second permanent remote monitor once the patient reaches the new destination. Alternatively, the display on the device could be used during transport, obviating the need for a separate transport monitor. The data could also be directly transmitted to an alternate wireless device, such as a PDA device, without the need for a dongle. Special software could register the disposable pressure sensor to the dongle or device to avoid cross-talk between multiple pressure sensor/wireless receiver units. Alternatively, the dongle and pressure sensor could come together in a disposable pouch and be pre-registered to avoid cross-talk or other type of interference.

Devices can be configured for a single application or for multiple different applications. A device may include a button or switch to allow the device algorithm and display to transition from different units of measurements, output configurations, graphical displays and/or one indication to the next. This transition might include scaling the bar graph, changing the display units (e.g. from mm Hg to cm $H_2O$), changing the display rate, etc, An indicator will alert the user to what mode the device is in. Alternately, the device could automatically change modes by monitoring the pressure readings (e.g. autoscaling the bar graph or changing modes based on the magnitude of the pressure and/or the rate of change in the pressure). For example, a pressure changing from 60 mm Hg to 120 m Hg at 1 Hz might indicate entry into an artery, a pressure changing from 0 mm hg to 20 mm Hg at 1 Hz might indicate entry into a vein, and a constant pressure might indicate a compartment.

In yet another embodiment, the device can contain alert means, such as indicators (visual or audio) that trigger when certain pressure ranges are encountered, such as pressure ranges anticipated for entry into the vein or artery, or pressure reading ranges, threshold values, patterns, and the like. The alerts could also activate if the needle or catheter is removed from a pressurized fluid (e.g. a "needle dislodgement" indicator). The device can also have user set alerts and/or the device could have colored LED's (or distinct audio tones) that indicate certain pressure ranges (e.g. yellow for a first pressure range, green for a second range, and red for a third range).

In another embodiment the present invention further provide a kit, which can include one or more detection device components as described herein. A kit may be assembled for portability, as well as use in a medical or surgical setting, and the like. A kit typically includes a detection device of the present invention, and the detection device may be provided in a fully assembled, partially assembled, or non-assembled configuration. As indicated, a device of the present invention may be configured or of a design such that one or more components of the detection device or corresponding assembly have a limited or single use, or are replaceable. As such, a kit can include a detection device with one or more replacement or accessory components, such as one or more replacement needles, syringes, guidewires, catheters, etc. In another embodiment, a kit may be designed for a single use only. A kit may include pre-sterilized components or device(s), as well as sterilized packaging.

The components of the present invention may be sterilized (and will generally be sterilizable) by any of the well known sterilization techniques, depending on the type of material. Suitable sterilization techniques include heat sterilization, radiation sterilization, chemical/gas sterilization, and the like.

The specific dimensions of any of the detection devices, systems, and components thereof, of the present invention may vary depending upon the intended application, as may be apparent to those of skill in the art in view of the disclosure herein. For example, selected probe or needle size, design or dimensions will typically differ depending on intended use.

It will be understood that the examples and embodiments described herein are for illustrative purposes and that various modifications or changes in light thereof may be suggested to persons skilled in the art and are included within the spirit and purview of this application and scope of the appended claims. Moreover, different combinations of embodiments described herein are possible, and such combinations are considered part of the present invention. In addition, all features discussed in connection with any one embodiment herein can be readily adapted for use in other embodiments herein. The use of different terms or reference numerals for similar features in different embodiments does not necessarily imply differences other than those which may be expressly set forth. Accordingly, the present invention is intended to be described solely by reference to the appended claims, and not limited to the preferred embodiments disclosed herein.

What is claimed is:

1. A method of distinguishing between positioning of a probe in a vein or an artery of a patient, comprising:

providing a device comprising a housing having a proximal housing portion and a distal housing portion, the distal housing portion coupled to the probe, the device further comprising,
a pressure sensing system at least partially carried by the housing and comprising a processing unit coupled with a pressure sensor so as to receive a signal from the pressure sensor and determine from the signal a pressure value of an environment about a distal portion of the probe, and
an output unit carried by the housing intermediate the proximal housing portion and the distal housing portion, the output unit comprising a visual display, the output unit coupled to the pressure sensing system so as to receive a pressure value signal and output on the visual display a reporting signal indicating the determined pressure value and/or positioning of the distal portion of the probe in the vein or the artery of the patient;
advancing the device distally such that the distal portion of the probe advances through tissue of the patient and into the vein of the patient;
detecting a change in pressure about the distal portion of the probe during advancing so as to indicate positioning of the distal portion of the probe;
distinguishing between positioning of the distal portion in the vein of the patient in response to the reporting signal on the visual display;
introducing a guidewire through the housing proximally to distally generally align with the probe into the vein following distinguishing of probe positioning, wherein the guidewire extends out a distal end of the probe; and
drawing blood toward a syringe coupled to the proximal housing portion of the housing for blood visualization.

2. The method of claim 1, wherein the probe is rigidly coupled to the device so as to allow positioning of probe by position manipulation of the device housing by a user; wherein advancing includes advancing a probe tip of the probe through the tissue of the patient, wherein detecting a change in pressure includes transmitting pressure from the probe tip through a bore in the probe to the pressure sensing system; and wherein advancing includes positioning the output unit adjacent a patient's body during advancing so that the output unit is in a line of sight by the user advancing the device.

3. The method of claim 1, wherein the probe is directly coupled to the device.

4. The method of claim 1, wherein the vein is an internal jugular vein, a subclavian vein, or a femoral vein.

5. The method of claim 1, further comprising detecting an increase in pressure upon probe entry into the vein and discontinuing advancement.

6. The method of claim 1, further comprising detecting an increase of pressure indicating that the probe has entered an artery, and altering device advancement based on the detected pressure.

7. The method of claim 1, further comprising withdrawing the probe and the housing while leaving the guidewire and introducing a catheter over the guidewire and into the patient's vein.

8. The method of claim 1, the device further comprising a guidewire port carried by the housing, extending to a proximal side of the housing and fluidly coupled to the distal portion coupled probe, and wherein the guidewire port is fluidly sealed proximally to the pressure sensor, further comprising inserting the guidewire through the guidewire port.

9. The method of claim 8, wherein inserting the guidewire through the guidewire port includes introducing the guidewire into the patient's vein through the coupled probe while measuring pressure at the distal end of the probe and with a syringe attached to the housing.

10. A device for distinguishing between positioning of a probe in a vein or an artery of a patient, the device comprising:
a housing having a proximal portion and a distal portion, the distal portion having a first port that is detachably couplable to the probe, the proximal portion of the housing comprising a second port that is detachably couplable to a syringe, and the first port fluidly coupled to the second port about a channel, wherein the channel is at least partially translucent exteriorly to the device so as to allow visualization of fluid within the channel;
a pressure sensing system at least partially carried by the housing and comprising a processing unit coupled with a pressure sensor so as to receive a signal from the pressure sensor and determine from the signal a pressure value of an environment about a distal portion of the probe;
an output unit carried by the housing intermediate the proximal portion and the distal portion, the output unit comprising a visual display, the output unit coupled to the pressure sensing system so as to receive pressure value signal and provide an output on the visual display comprising a reporting signal indicating at least one of the determined pressure value, a position of the probe in a vein or artery of the patient, or both, wherein the output on the display distinguishes between placement of the distal portion in the artery or the vein; and
a guidewire port carried by the housing and fluidly coupled to the first port wherein the syringe is coupled to the second port such that the probe, device, and syringe are arranged axially and in sequence from the distal portion to the proximal portion.

11. The device of claim 10, wherein the guidewire port is fluidly coupled to the channel with a frangible seal to allow a guidewire therethrough into a patient out a distal end of the probe with the pressure sensing system sensing pressure while inserting the guidewire into the vein without disconnecting the housing from either the probe or the syringe.

12. The device of claim 10, wherein the pressure sensing unit is in operable communication with the channel.

13. The device of claim 10, wherein the probe comprises a needle.

14. The device of claim 10, wherein the visual display is angled proximally within and by the housing and relative to the proximal portion of the housing.

15. The device of claim 10, the reporting signal output via the display comprising at least two different readings indicative of average pressures each measured over a time period having different length of time, frequency of pressure reading, or both.

16. The device of claim 10, the reporting signal output via the display comprising a numerical pressure reading and a non-numerical pressure reading having a waveform graph.

17. The device of claim 10, wherein the reporting signal output via the display comprises a non-numerical pressure reading comprising bar graph image.

18. An assembly for distinguishing between positioning of a probe in a vein or an artery of a patient, the assembly comprising:
a device comprising a housing having a distal portion with a first port that is detachably coupled to the probe and a proximal portion with a second port detachably coupled to a syringe, and a third port to receive a guidewire and connected to the first port to form a path for extending the guidewire through the housing and the probe into a vein;

a pressure sensing system carried by the housing and comprising a processing unit coupled with a pressure sensor so as to receive signal from the pressure sensor and determine from the received signal a pressure value of an environment about a distal portion of the probe; and an output unit carried by the housing, the output unit comprising a visual display, the output unit coupled to the pressure sensing system so as to receive a pressure value signal and provide an output on the visual display comprising a reporting signal indicating the positioning of the probe in a vein or artery of the patient, wherein the output on the display distinguishes between placement of the distal portion in the artery or the vein, the reporting signal output via the display comprising at least two different readings indicative of average pressures each measured over a time period having different length of time, frequency of pressure reading, or both;

wherein the pressure sensing system and the output unit are disposed substantially between the distal and proximal portions of the housing.

19. The assembly of claim 18, wherein the probe, housing and syringe are assembled substantially in an axial arrangement with the visual display being intermediate the probe and the second port of the housing.

20. The assembly of claim 18, wherein the visual display is intermediate the distal and proximal portions of the housing.

21. The assembly of claim 18, wherein the housing is adapted to be held in a single hand by a user.

22. The assembly of claim 18, wherein the pressure sensing system and the output unit are disposed substantially between the first port and the second port.

\* \* \* \* \*